United States Patent
Sauvé et al.

(10) Patent No.: US 6,638,921 B1
(45) Date of Patent: Oct. 28, 2003

(54) PYRIDOXAL-5-PHOSPHATE DERIVATIVES AS HIV INTEGRASE INHIBITORS

(75) Inventors: Gilles Sauvé, Laval (CA); Brent Richard Stranix, Pointe-Claire (CA)

(73) Assignee: Pharmacor Inc., Laval (CA)

( * ) Notice: Subject to any disclaimer, the term of this patent is extended or adjusted under 35 U.S.C. 154(b) by 0 days.

(21) Appl. No.: 10/183,468

(22) Filed: Jun. 28, 2002

(30) Foreign Application Priority Data

Mar. 28, 2002 (CA) .............................. 2379526

(51) Int. Cl.[7] .............................. A61K 31/06; C07F 9/58
(52) U.S. Cl. ........................................ 514/150; 534/771
(58) Field of Search ............................ 534/771; 514/150

(56) References Cited

PUBLICATIONS

Ziganshin et al., Chemical Abstracts, 130:93191, 1998.*
Lasky, L. A. et al., Cell (1997) vol. 50, pp. 975–985.
Haseltine, W. A., Faseb J. (1991) vol. 5, pp 2349–2360.
Goff S. P., J. Acq. Imm. Defic. Syndr. (1990) vol. 3, pp. 817–831.
Bukrinsky, M. I., Proc. Natn. Acad. Sci. USA (1992) vol. 89, pp.6580–6584.
Gallay, P., et al., Cell (1993) vol. 80, pp. 379–388.
Sakai, H. J. Virol. (1993) vol. 67, pp. 1169–1174.
Burke, Jr. T. R. et al., J. Med. Chem. (1995) vol. 38, pp. 4171–4178.
A.J. Japour et al. Antimicrobial Agents and Chemotherapy, vol. 37 (1993) p. 1095–1101.
R. Pauwels et al. Journal of Virological Methods, vol. 20 (1988) p. 309–321.

* cited by examiner

*Primary Examiner*—Fiona T. Powers
(74) *Attorney, Agent, or Firm*—Ronald S. Kosie; Robert Brouillette; Gaetan Princ

(57) ABSTRACT

A compound of formula I

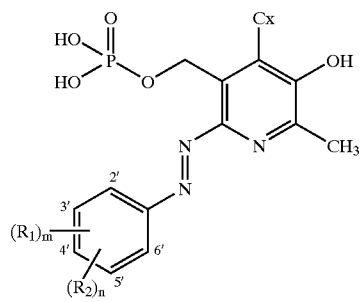

and pharmaceutically acceptable derivatives thereof Cx, $R_1$ and $R_2$ being as defined in the disclosure may be used to inhibit the activity of HIV integrase.

38 Claims, No Drawings

PYRIDOXAL-5-PHOSPHATE DERIVATIVES AS HIV INTEGRASE INHIBITORS

TECHNICAL FIELD OF THE INVENTION

The present invention relates to a series of novel pyridoxal derivatives which have HIV integrase inhibitory properties that have been characterized by specific structural and physicochemical features. This inhibitory property may be advantageously used to provide compounds with antiviral properties against HIV viruses, including the HIV-1 and HIV-2 viruses. The pyridoxal derivatives including pharmaceutical compositions thereof may be used to inhibit the activity of HIV integrase.

BACKGROUND OF THE INVENTION

The HIV (human immunodeficiency virus) retrovirus is the causative agent for AIDS (acquired immunodeficiency syndrome). Thus the HIV-1 retrovirus primarily uses the CD4 receptor (a 58 kDa transmembrane protein) to gain entry into cells, through high-affinity interactions between the viral envelope glycoprotein (gp 120) and a specific region of the CD4 molecule found in CD4 (+) T-helper lymphocytes and certain other cells (Lasky L. A. et al., Cell vol. 50, p. 975–985 (1987)). HIV infection is characterized by a period immediately following infection called "asymptomatic" which is devoid of clinical manifestations in the patient. Progressive HIV-induced destruction of the immune system then leads to increased susceptibility to opportunistic infections, which eventually produces a syndrome called AIDS-related complex (ARC) characterized by symptoms such as persistent generalized lymphadenopathy, fever, weight loss, followed itself by full blown AIDS. After entry of the retrovirus into a cell, viral RNA is converted into DNA, which is then integrated into the host cell DNA. The reverse transcriptase encoded by the virus genome catalyzes the first of these reactions (Haseltine W. A. FASEB J. vol 5, p. 2349–2360 (1991)). At least three functions have been attributed to the reverse transcriptase: RNA-dependent DNA polymerase activity which catalyzes the synthesis of the minus strand DNA from viral RNA, ribonuclease H (RNase H) activity which cleaves the RNA template from RNA-DNA hybrids and DNA-dependent DNA polymerase activity which catalyzes the synthesis of a second DNA strand from the minus strand DNA template (Goff S. P. J. Acq. Imm. Defic. Syndr. Vol 3, p. 817–831 (1990)). At the end of reverse transcription, the viral genome now in the form of DNA (called provirus) is integrated into host genomic DNA and serves as a template for viral gene expression by the host transcription system, which leads eventually to virus replication (Roth et al.,1989). The preintegration complex consists of integrase, reverse transcriptase, p17 and proviral DNA (Bukrinsky M. I., Proc. Natn. Acad. Sci. USA vol. 89 p.6580–6584 (1992)). The phosphorylated p17 protein plays a key role in targeting the preintegration complex into the nucleus of the host cell (Gallay et al., 1995).

The primary RNA transcripts made from the provirus are synthesized by the host cell RNA polymerase II which is modulated by two virus-encoded proteins called tat and rev. The viral proteins are formed as polyproteins.

Post-translational modifications of viral polyproteins include processing and glycosylation of Env (envelope) proteins, and myristylation of the N-terminal residue of the p17 protein in the Gag and Gag-Pol polyproteins. The viral protease is involved in processing polyproteins Gag and Gag-Pol into mature proteins, an essential step for virus infectivity.

A number of synthetic antiviral agents have been designed to block various stages in the replication cycle of HIV. These agents include compounds which interfere with viral binding to CD4 (+) T-lymphocytes (for example, soluble CD4), compounds which block viral reverse transcriptase (for example, didanosine and zidovudine (AZT)), budding of virion from the cell (interferon), or the viral protease (for example Ritonavir and Indinavir). Some of these agents proved ineffective in clinical tests. Others, targeting primarily early stages of viral replication, have no effect on the production of infectious virions in chronically infected cells. Furthermore, administration of many of these agents in effective therapeutic doses has led to cell-toxicity and unwanted side effects, such as anemia, neurotoxicity and bone marrow suppression. Anti-protease compounds in their present form are typically large and complex molecules of peptidic nature that tend to exhibit poor bioavailability and are not generally consistent with oral administration. These compounds often exhibit side effects such as nausea, diarrhea, liver abnormalities and kidney stones.

None of the known antiviral agents on the market target the HIV integrase. Accordingly, the need exists for compounds that can effectively inhibit the action of this viral enzyme and that can be used for treating HIV infections.

The terms HIV integrase and integrase as used herein are used interchangeably and refer to the integrase enzyme encoded by the human immunodeficiency virus type 1 or 2. In particular this term includes the human immunodeficiency virus type 1 integrase.

SUMMARY OF THE INVENTION

The present invention relates to a class of pyridoxal compounds as well as their pharmaceutically acceptable derivatives (e.g., salts).

Accordingly, the present invention in accordance with one aspect thereof provides a compound of formula I

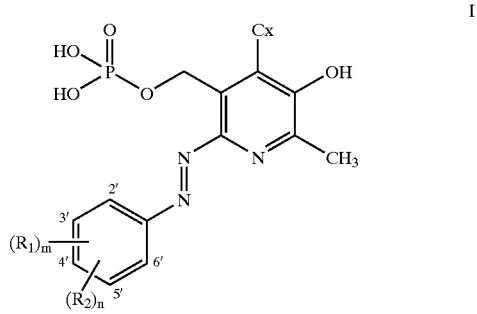

and pharmaceutically acceptable derivatives thereof including where applicable or appropriate pharmaceutically acceptable salts thereof, wherein Cx may be selected from the group consisting of —CH=O, —CH=N—OH and —CH(OCH$_2$CH$_3$)$_2$, wherein R$_1$ may be selected from the group consisting of H, a straight alkyl group of 1 to 6 carbon atoms, a branched alkyl group of 3 to 6 carbon atoms, F, Cl, Br, I, —CN and —COOH, wherein R$_2$ may be selected from the group consisting of —COOH, —SO$_2$NR$_3$R$_4$, —SO$_2$R$_5$, —CONR$_3$R$_4$ and —COR$_5$, wherein R$_3$ may be selected from the group consisting of H, a straight alkyl group of 1 to 6 carbon atoms, and a branched alkyl group of 3 to 6 carbon atoms, wherein R$_4$ may be selected from the group consisting of H, a straight alkyl group of 1 to 6 carbon atoms, a branched alkyl group of 3 to 6 carbon atoms, a cycloalkyl group of 3 to 8 carbon atoms, adamantan- 1-yl, —CH$_2$CH$_2$OH, pyridin-2-yl, pyridin-3-yl, pyridin-4-yl, 1,2,3,4-tetrahydroquinolin-5-yl, isoquinolin-5-yl, isoazol-3-yl, 2-halogeno-phenyl, 3-halogeno-phenyl, 4-halogeno-phenyl (halogeno being F, Cl, Br or I), 1,4,5,6-tetrahydropyrimidin-2-yl, pyrimidin-2-yl, 2,6-dimethylpyrimidin-4-yl, thiazol-2-yl, and a group of formula,

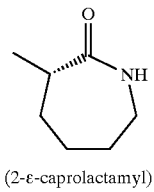

(2-ε-caprolactamyl)

wherein R$_5$ may be selected from the group consisting of aziridinyl, azetidinyl, pyrrolidinyl, piperidinyl, azepanyl, azocanyl (i.e., the azacycloalkanes, 3 to 8 member ring systems containing at least one nitrogen ring atom) and morpholinyl, with the proviso that the R$_5$ group is linked to the adjacent sulfur atom at or via a ring nitrogen atom thereof (e.g. R$_5$ may be selected from among aziridin-1-yl, azetidin-1-yl, pyrrolidin-1-yl, piperidin-1-yl, azepan-1-yl, morpholin-4-yl, etc.) and wherein m may be 0, 1, 2 or 3, wherein n may be 0 or 1.

Azepan-1-yl has the following structure:

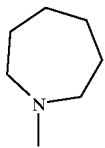

In a further aspect, the present invention provides, a compound(s) of formula IA

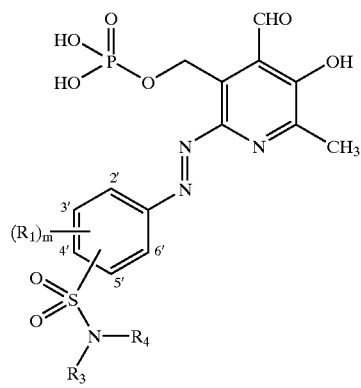

IA and pharmaceutically acceptable derivatives thereof including where applicable or appropriate pharmaceutically acceptable salts thereof, wherein R$_1$ may be H, wherein R$_3$ may be selected from the group consisting of H, a straight alkyl group of 1 to 6 carbon atoms, and branched alkyl group of 3 to 6 carbon atoms, and wherein R$_4$ may be selected from the group consisting of H, a straight alkyl group of 1 to 6 carbon atoms, a branched alkyl group of 3 to 6 carbon atoms, a cycloalkyl group of 3 to 8 carbon atoms, adamantan-1-yl, —CH$_2$CH$_2$OH, pyridin-2-yl, pyridin-3-yl, pyridin-4-yl, 1,2,3,4-tetrahydroquinolin-5-yl, isoquinolin-5-yl, isoazol-3-yl, 2-halogeno-phenyl, 3-halogeno-phenyl, 4-halogeno-phenyl (halogeno being F, Cl, Br or I), 1,4,5,6-tetrahydropyrimidin-2-yl, pyrimidin-2-yl, 2,6-dimethylpyrimidin-4-yl, thiazol-2-yl, and a group of formula,

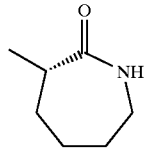

(2-ε-caprolactamyl)

and wherein m may be 1.

In an additional aspect, the present invention provides, a compound(s) of formula IB,

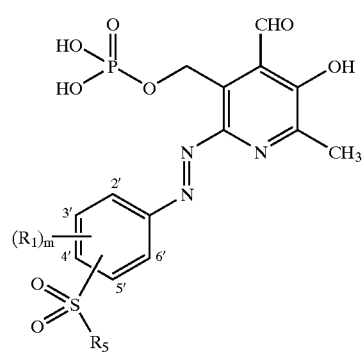

IB and pharmaceutically acceptable derivatives thereof including where applicable or appropriate pharmaceutically acceptable salts thereof, wherein R$_1$ may be H.

wherein R$_5$ may be selected from the group consisting of pyrrolidin-1-yl, piperidin-1-yl and morpholin-4-yl, and wherein m may be 1.

In another aspect, the present invention provides, a compound(s) of formula IC,

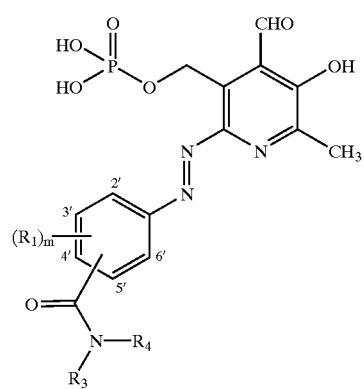

IC wherein $R_1$ may be H, wherein $R_3$ may be selected from the group consisting of H, a straight alkyl group of 1 to 6 carbon atoms, and a branched alkyl group of 3 to 6 carbon atoms, and wherein $R_4$ may be selected from the group consisting of H, a straight alkyl group of 1 to 6 carbon atoms, a branched alkyl group of 3 to 6 carbon atoms, a cycloalkyl group of 3 to 8 carbon atoms, adamantan-1-yl, —CH$_2$CH$_2$OH, pyridin-2-yl, pyridin-3-yl, pyridin-4-yl, 1,2,3,4-tetrahydroquinolin-5-yl, isoquinolin-5-yl, isoazol-3-yl, 2-halogeno-phenyl, 3-halogeno-phenyl, 4-halogeno-phenyl (halogeno being F, Cl, Br or I), 1,4,5,6-tetrahydropyrimidin-2-yl, pyrimidin-2-yl, 2,6-dimethylpyrimidin-4-yl, thiazol-2-yl, and a group of formula,

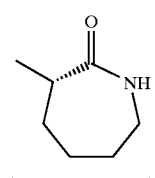

(2-ε-caprolactamyl)

and wherein m may be 1.

In yet another aspect, the present invention provides, a compound(s) of formula ID,

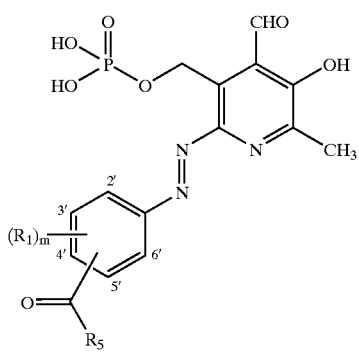

ID and pharmaceutically acceptable derivatives thereof including where applicable or appropriate pharmaceutically acceptable salts thereof, wherein $R_1$ may be H, wherein $R_5$ may be selected from the group consisting of pyrrolidin-1-yl, piperidin-1-yl and morpholin-4-yl, and wherein m may be 1.

The compounds of this invention include pharmaceutically acceptable derivatives of the compounds of formula I (as well as of formulae IA, IB, IC and ID) as defined above. A "pharmaceutically acceptable derivative" means any pharmaceutically acceptable salt (e.g., Na, K, Cs, etc), acetals (i.e., dimethylacetal, diethylacetal, etc), oxime, or ester (as for example, but not limited to methyl, ethyl, propyl, isopropyl esters, etc) of a compound of this invention. Thus salts derived from appropriate bases include alkali metal (e.g., sodium), alkaline earth metal (e.g., magnesium), ammonium and N—(C$_{1-4}$ alkyl)$_4^+$ salts.

Furthermore, the expression "pharmaceutically acceptable derivative" is to be understood as referring to any other compound having a structure such that, upon administration to a recipient, it is capable of providing (directly or indirectly) a compound of this invention or an antivirally active metabolite or residue thereof. Thus the compounds of this invention may be modified by appending appropriate functionalities to enhance selective biological properties. Such modifications are known in the art and include those which increase biological penetration into a given biological system (e.g., blood, lymphatic system, central nervous system), increase oral bioavailability, increase solubility to allow administration by injection, alter metabolism and alter rate of excretion.

The compounds of the present invention including where applicable their pharmaceutically acceptable derivatives have an affinity for integrase, in particular, HIV integrase. Therefore, these compounds are useful as inhibitors of such integrase, i.e. they are in particular useful as HIV integrase inhibitors. These compounds can be used alone or in combination with other therapeutic or prophylactic agents, such as antivirals, antibiotics, immunomodulators or vaccines, for the treatment or prophylaxis of viral infection.

According to the present invention, the compounds of this invention are capable of inhibiting HIV viral replication in human CD4+ T-cells, by inhibiting the ability of HIV integrase to integrate the double stranded DNA into host genomic DNA for further virus replication by the host cell machinery (Sakai H., J. Virol. Vol. 67 p. 1169–1174 (1993)). These novel compounds can thus serve to reduce the production of infectious virions from acutely infected cells, and can inhibit the initial or further infection of host cells. Accordingly, these compounds are useful as therapeutic and prophylactic agents to treat or prevent infection by HIV-1 and related viruses, which may result in asymptomatic HIV-1 infection, AIDS-related complex (ARC), acquired immunodeficiency syndrome (AIDS), AIDS-related dementia, or similar diseases of the immune system.

This invention also provides in a further aspect, pharmaceutical compositions comprising a pharmaceutically acceptable carrier and at least one compound of formulae I, IA, IB, IC and ID as defined herein. The pharmaceutical composition may comprise, for example, a pharmaceutically effective amount of such one or more compounds of this invention. The pharmaceutical compositions may be used to inhibit integrase, including HIV integrase, thus providing protection against HIV infection.

The term "pharmaceutically effective amount" refers to an amount effective in treating HIV infection in a patient. It is also to be understood herein that a "pharmaceutically effective amount" may be interpreted as an amount giving a desired therapeutic effect, either taken into one dose or in any dosage or route or taken alone or in combination with other therapeutic agents. In the case of the present invention, a "pharmaceutically effective amount" may be understood as an amount having an inhibitory effect on HIV (HIV-1 and HIV-2 as well as related viruses (e.g., HTLV-I and HTLV-II, and simian immunodeficiency virus) infection cycle (e.g., inhibition of replication, reinfection, maturation, budding etc.) and on any organism depending on integrase for their life cycle.

The term "prophylactically effective amount" refers to an amount effective in preventing HIV infection in a patient. As used herein, the term "patient" refers to a mammal, including a human.

The terms "pharmaceutically acceptable carrier", "pharmaceutically acceptable adjuvant" and "physiologically acceptable vehicle" refer to a non-toxic carrier or adjuvant that may be administered to a patient, together with a compound of this invention, and which does not destroy the pharmacological activity thereof.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

It is to be understood herein, that if a "range", "group of substances" or particular characteristic (e.g., temperature, concentration, time and the like) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to the number of carbon atoms, the mention of the range of 1 to 6 carbon atoms is to be understood herein as incorporating each and every individual number of carbon atoms as well as sub-ranges such as, for example, 1 carbon atoms, 3 carbon atoms, 4 to 6 carbon atoms, etc.

with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;

and similarly with respect to other parameters such as concentrations, elements, etc. . . .

It is thus to be understood herein that a "straight alkyl group of 1 to 6 carbon atoms" includes for example, methyl, ethyl, propyl, butyl, pentyl, hexyl.

It is further to be understood herein that a "branched alkyl group of 3 to 6 carbon atoms" includes for example, without limitation, iso-butyl, tert-butyl, 2-pentyl (i.e. 2-methyl-butyl), 3-pentyl (i.e. 3-methyl-butyl; isopentyl), neopentyl, tert-pentyl, etc.

It is also to be understood herein, that a "cycloalkyl group having 3 to 6 carbon" includes for example, without limitation, cyclopropyl, cyclobutyl, cyclopentyl, cyclocyclohexyl (i.e., $C_6H_{11}$).

It is in particular to be understood herein that the compound formulae each include each and very individual compound described thereby as well as each and every possible class or sub-group or sub-class of compounds whether such class or sub-class is defined as positively including particular compounds, as excluding particular compounds or a combination thereof; for example an exclusionary definition for the formulae (e.g. I) may read as follows: "provided that when one of $R_1$ and $R_2$ is —COOH and the other is H, —COOH may not occupy the 4' position".

It is also to be understood herein that "g" or "gm" is a reference to the gram weight unit and "C", or "° C." is a reference to the Celsius temperature unit.

The compounds of this invention may be readily prepared using conventional techniques from commercially available and cheap starting materials. In general, the derivatives of the present invention may be readily obtained from pyridoxal-5-phosphate through sequences recognized by those knowledgeable in the art as straightforward, requiring readily available reagents and easy techniques. Using standard techniques, pyridoxal-5-phosphate may be transformed to the desired HIV integrase inhibitors according to approaches as shown in schemes 3 and 4 which are discussed below. Schemes 1 and 2 show the preparation of aminoaryl carboxamides (Scheme 1) as well as m- and p-aminoaryl sulfonamides (Scheme 2) which are used in the preparation of HIV integrase inhibitors.

Scheme 1 illustrates a generic example for the preparation of aminoaryl carboxamides 3.

As shown on Scheme 1, commercially available o-, m- or p-nitrobenzoyl chloride 1 are easily transformed into the corresponding amide 2 upon treatment with an amine ($R_3R_4NH$) in a mixture of acetone and pyridine. Subsequently, the nitro group is reduced by catalytic hydrogenation using 10% Pd/C as catalyst in MeOH, to give the amine 3. The average yield of this two step sequence is 70%. The amine ($R_3R_4NH$) can easily be replaced by an Azacycloalkyl ($C_3$–$C_8$) or by an Aryl-$NH_2$ to lead to derivatives 2' or 2".

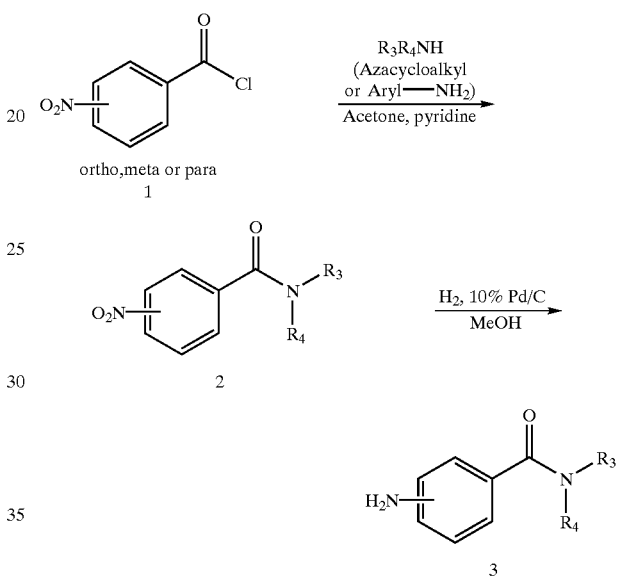

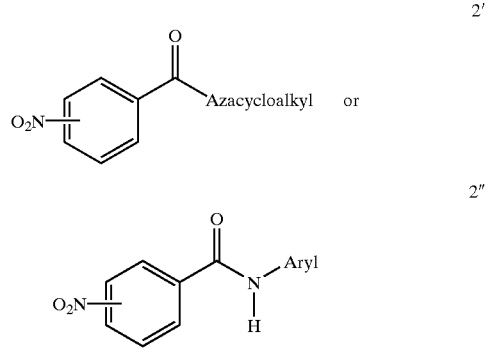

Scheme 2 illustrates a generic example for the preparation of p-aminoaryl sulfonamides 6 or m-aminoaryl sulfonamides 7.

As shown on Scheme 2, commercially available 4-acetamidobenzenesulfonyl chloride 4 is coupled with an amine ($R_3R_4NH$) to give the sulfonamide 5 in 85% yield. Hydrolysis of the acetamide function upon treatment with hydrochloric acid at reflux for 10 minutes lead to the corresponding p-aminoaryl sulfonamides 6 in 95% average yield.

Scheme 2

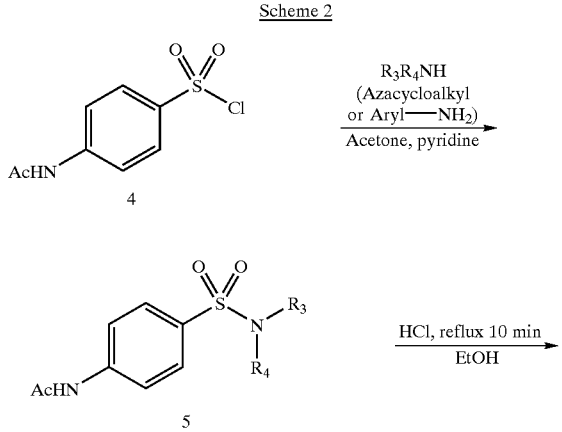

$R_3R_4NH$ may as shown above be replaced by an Azacycloalkyl ($C_3$–$C_8$) or by an Aryl—$NH_2$ to lead to intermediate derivatives 5' or 5": (see below) which may in turn be converted to corresponding aminophenyl compounds 6' and 6" (not shown).

Using a similar reaction sequence, starting with m-nitrobenzenesulfonyl choride followed by catalytic hydrogenation for the second step, the analogues m-aminobenzene sulfonamides (7, 7' or 7") can be obtained (see experimental section).

Scheme 3 illustrates a generic example for the coupling of aminoaryl carboxamides 3 with pyridoxal-5-phosphate.

Diazotation of an appropriate aminoaryl carboxamide 3 (i.e., ortho, meta or para) upon treatment with $NaNO_2$ and hydrochloric acid gave the corresponding diazonium salt intermediate (3-$N_2^+Cl^-$) which is immediately added to a basic solution of pyridoxal-5-phosphate. The resulting reaction mixture gave compound 8 in 65% average yield.

Scheme 3

Derivatives 3' or 3" can be treated in the same fashion as compound 3.

Scheme 4 illustrates a generic example for the coupling of p-aminoaryl sulfonamide 6 (or m-aminoaryl sulfonamide 7) with pyridoxal-5-phosphate.

Diazotation of an appropriate p-aminoaryl sulfonamide 6 (or m-aminoaryl sulfonamide 7) upon treatment with $NaNO_2$ and hydrochloric acid gave the corresponding diazonium salt intermediate ($N_2^+Cl^-$) which is immediately added to a basic solution of pyridoxal-5-phosphate. The resulting reaction mixture lead to compound 9 in 65% average yield.

Scheme 4

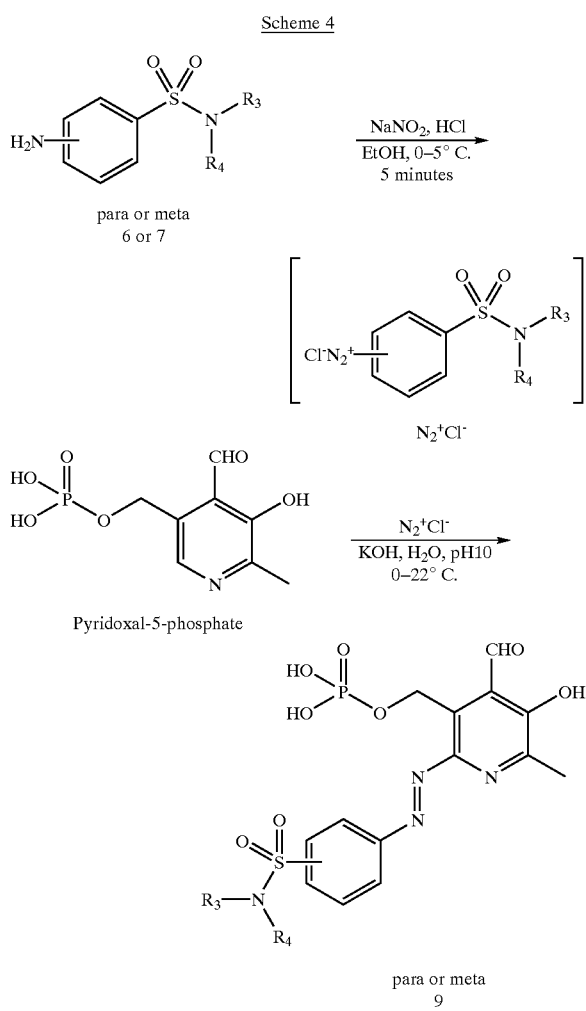

para or meta
6 or 7

Pyridoxal-5-phosphate para or meta
9

Derivatives 6' or 6" (para) and 7' or 7" (meta) can be treated in the same fashion as compound 6 (para) or 7 (meta).

The diazo derivatives are known to exist in two geometric isomers (cis and trans) which can be present in our compounds. However, the trans isomer is either the sole or the major isomer.

As can be appreciated by the skilled artisan, the above synthetic schemes are not intended to comprise a comprehensive list of all means by which the compounds described and claimed in this application may be synthesized. Further methods will be evident to those of ordinary skill in the art.

The novel compounds of the present invention are excellent ligands for integrase, particularly HIV-1, and most likely HIV-2 and HTLV-1 integrase. Accordingly, these compounds are capable of targeting and inhibiting an early stage event in the replication, i.e. the integration of viral DNA into the human genome, thus preventing the replication of the virus.

In addition to their use in the prophylaxis or treatment of HIV infection, the compounds according to this invention may also be used as inhibitory or interruptive agents for other viruses which depend on integrases, similar to HIV integrases, for obligatory events in their life cycle. Such compounds inhibit the viral replication cycle by inhibiting integrase. Because integrase is essential for the production of mature virions, inhibition of that process effectively blocks the spread of virus by inhibiting the production and reproduction of infectious virions, particularly from acutely infected cells. The compounds of this invention advantageously inhibit enzymatic activity of integrase and inhibit the ability of integrase to catalyze the integration of the virus into the genome of human cells.

The compounds of this invention may be employed in a conventional manner for the treatment or prevention of infection by HIV and other viruses which depend on integrases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection. Also, a compound of this invention may be combined with pharmaceutically acceptable adjuvants conventionally employed in vaccines and administered in prophylactically effective amounts to protect individuals over an extended period of time against viral infections, such as HIV infection. As such, the novel integrase inhibitors of this invention can be administered as agents for treating or preventing viral infections, including HIV infection, in a mammal. The compounds of this invention may be administered to a healthy or HIV-infected patient either as a single agent or in combination with other antiviral agents which interfere with the replication cycle of HIV. By administering the compounds of this invention with other antiviral agents which target different events in the viral replication cycle, the therapeutic effect of these compounds is potentiated. For instance, the co-administered antiviral agent can be one which targets early events in the life cycle of the virus, such as cell entry, reverse transcription and viral DNA integration into cellular DNA. Antiviral agents targeting such early life cycle events include, didanosine (ddi), zalcitabine (ddC), stavudine (d4T), zidovudine (AZT), polysulfated polysaccharides, sT4 (soluble CD4)—which blocks attachment or adsorption of the virus to host cells—and other compounds which block binding of virus to CD4 receptors on CD4-bearing T-lymphocytes. Other retroviral reverse transcriptase inhibitors, such as derivatives of AZT, may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformiate, eflornithine, ribavirin, acyclovir, alpha interferon and trimenotrexate. Additionally, non-ribonucleoside inhibitors of reverse transcriptase, such as TIBO, nevirapine or delavirdine, may be used to potentiate the effect of the compounds of this invention, as may viral uncoating inhibitors, inhibitors of trans-activating proteins such as tat or rev, or inhibitors of the viral protease. These compounds may also be co-administered with other inhibitors of HIV integrase.

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity. Preferred combination therapies include the administration of a compound of this invention with AZT, 3TC, ddI, ddC, d4T, combivir, ziagen, sustiva, nevirapine and delavirdine.

Alternatively, the compounds of this invention may also be co-administered with other HIV protease inhibitors such as saquinavir, indinavir, nelfinavir, ritonavir and amprenavir to increase the effect of therapy or prophylaxis against various viral mutants or members of other HIV quasi species.

We prefer administering the compounds of this invention as single agents or in combination with retroviral reverse transcriptase inhibitors, such as derivatives of AZT or HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbante, tumor necrosis factor, naltrexone and rEPO); antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an integrase inhibitor of this invention and another therapeutic or prophylactic agent.

Although this invention focuses on the use of the compounds disclosed herein for preventing and treating HIV infection, the compounds of this invention can also be used as inhibitory agents for other viruses that depend on similar integrases for obligatory events in their life cycle. These viruses include, but are not limited to, other diseases caused by retroviruses, such as simian immunodeficiency viruses, HTLV-I and HTLV-II.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solutions. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral and carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical compositions can be formulated with a suitable lotion or cream containing the active compound suspended or dissolved in a carrier. Suitable carriers include, but are not limited to mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 75% active compound (w/w). Preferably, such preparations contain from about 20% to about 50% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease, at least in principle. Patients may, however, require intermittent treatment on a long-term basis, upon any recurrence of disease symptoms, especially for AIDS.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to integrases, particularly HIV integrase. As commercial reagent, the compounds of this invention, and their derivatives, may be used to block integration of a target DNA molecule by integrase, or may be derivatized to bind to a stable resin as a tethered substrate for affinity chromatography applications. These and other uses which characterize commercial integrase inhibitors will be evident to those of ordinary skill in the art.

In the description herein, the following abbreviations are used:

| Abbreviation | Meaning |
| --- | --- |
| AcOH | Acetic acid |
| Ar | Argon |
| ARC | AIDS-related complex |
| AIDS | Acquired Immunodeficiency Syndrome |
| AZT | 3-Azido-3-deoxythymine (Zidovudine) |
| BSA | Bovine serum albumin |
| DABCYL | 4-[[4-(dimethylamino)phenyl]azo]benzoic acid |
| DCE | Dichloroethane |
| DMF | Dimethylformamide |
| DNA | Deoxyribonucleic acid |
| EtOH | Ethyl alcohol |
| g | gram |
| HPLC | High pressure liquid chromatography |
| HIV-1, -2 | Human immunodeficiency virus type 1, type 2 |
| HTLV-I, -II | Human T-cell lymphotropic virus type I, type II |
| IL-2 | Interleukine-2 |
| M | Molar |
| MeOH | Methyl alcohol |
| mg | Milligram |
| mp | Melting point |
| min | Minute |
| mL | Milliliter |
| mmol | Millimole |
| nM | Nanomolar |
| rEPO | Recombinant erythropoietin |
| RNA | Ribonucleic acid |
| 3TC | 2',3'-Dideoxy-3-thiacytidine |
| THF | Tetrahydrofuran |
| $IC_{50}$ | Inhibitory Concentration 50: the concentration of drug required to reduce the enzyme activity by 50%. |
| $EC_{50}$ | Effective Concentration 50: the concentration of drug required to reduce the virus' replication in cell culture by 50%. |
| $CCIC_{50}$ | Cell Culture Inhibitory Concentration 50: the concentration of drug required to reduce the cell survival by 50%. |

This section describes the synthesis of several molecules that are presented in this document. These examples are for the purpose of illustration only and are not to be construed as limiting the scope of the invention in any way. This section presents the detailed synthesis of compounds no. 1 to 53 of this invention.

Materials and Methods

Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and positive air pressure to allow proper rate of elution. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid followed by heating. Alternatively, analytical plates can be treated with a 0.3% ninhydrin solution in ethanol containing 3% acetic acid and/or a CAM solution made of 20 g $(NH_4)_6Mo_7O_{24}$ and 8.3 g $Ce(SO_4)_2$ polyhydrate in water (750 mL) containing concentrated sulfuric acid (90 mL).

Unless otherwise indicated, all starting materials were purchased from a commercial source such as Aldrich Co. or Sigma Co.

Melting points (mp) were determined on a Büichi 530 melting point apparatus in capillary tubes and were uncorrected.

Optical rotations ($[\alpha]_D^t$) were measured using a Jasco DIP-370 digital polarimeter at 589 nm (the D line of sodium). Specific rotation is calculated from the observed rotation according to the expression:

$$[\alpha]_D^t = 100\alpha/l \cdot c.$$

where

[α]$_D$=specific rotation,

α=observed rotation, c=concentration of the sample in grams per 100 mL of solution, l=the length of the polarimeter tube in decimeters, t=temperature (° C.).

Mass spectra were recorded on a Hewlett Packard LC/MSD 1100 system APCI either in negative mode or positive mode.

Nuclear magnetic resonance (NMR) spectra were recorded on a Bruker AMX 500 equipped with a reversed or QNP probe. Samples were dissolved in deuterochloroform ($CDCl_3$), deuterium oxide ($D_2O$) or deuterodimethylsulfoxide (DMSO-$d_6$) for data acquisition using tetramethylsilane as internal standard. Chemical shifts (δ) are expressed in parts per million (ppm), the coupling constants (J) are expressed in hertz (Hz) whereas multiplicities are denoted as s for singlet, d for doublet, dd for doublet of doublets, t for triplet, q for quartet, quint for quintet m for multiplet, and br s for broad singlet.

GENERAL PROCEDURES

A. Synthesis of Aminoaryl Carboxamides

Step 1. Formation of Nitroaryl Carboxamides.

10 mmol of an aryl or alkyl amine is dissolved in 50 mL acetone with 2 mL pyridine and added dropwise to a solution of 10 mmol of a ortho-, meta- or para-nitrobenzoyl chloride. The solution is left to stand 12 h and, in most cases, the precipitated amide is collected. Otherwise, the solution is poured in ice water containing 3 eq. of HCl and extracted with ethyl acetate. The organic fraction is dried with $MgSO_4$ and evaporated to yield the desired product.

Step 2. Formation of Aminoaryl Carboxamides 5 mmol of the nitroarylcarboxamide is dissolved in argon (Ar) saturated MeOH and 200 mg of 10% Pd/C is added. A balloon of $H_2$ gas is then connected via a needle and left to stir for 1–8 h. The solution is purged with Ar again and filtered through celite to remove the Pd/C. The solution is then evaporated to yield the corresponding amine (>65% two steps).

B. Synthesis of p-Aminoaryl Sulfonamides

Step 1. Formation of N-Aryl or N-Alkyl p-Acetamidoaryl Sulfonamides.

10 mmol of an aryl or alkyl amine is dissolved in 50 mL acetone with 2 mL pyridine and added dropwise to a solution of 10 mmol of a p-acetamidobenzensulfonyl chloride. The solution is left to stand 12 h and, in most cases, the precipitated amide is collected. Otherwise the solution is poured in ice water containing 3 eq. of HCl and extracted with ethyl acetate. The organic fraction is dried with $MgSO_4$ and evaporated to yield the desired product.

Step 2. Formation of p-Aminoaryl Sulfonamides 5 mmol of the acetamide is dissolved in 20 mL EtOH. Afterwards, 5 mL concentrated HCl is added and the mixture is refluxed for 10 min. The solution is then left to cool in ice whereupon a white precipitate is formed. The precipitated aminoaryl sulfonamide hydrochloride is filtered off and used as such without further purification (>65% two steps).

C. Synthesis of m-Aminoaryl Sulfonamides

Step 1. Formation of m-N-(Aryl or Alkyl) Nitroaryl Sulfonamides.

10 mmol of an aryl or alkyl amine is dissolved in 50 mL acetone with 2 mL pyridine and added dropwise to a solution of 10 mmol of a m-nitrobenzenesulfonyl chloride. The solution is left to stand 12 h and in most cases the precipitated amide is collected. Otherwise the solution is poured in ice water containing 3 eq. of HCl and extracted with ethyl acetate. The organic fraction is dried with $MgSO_4$ and evaporated to yield the desired product.

Step 2. Formation of m-Aminoaryl Sulfonamides 5 mmol of the nitroarylsulfonamide is dissolved in Ar saturated MeOH and 200 mg of 10% Pd/C is added. A balloon of $H_2$ gas is then connected via a needle and left to stir for 1–8 h. The solution is purged with Ar again and filtered through celite to remove the Pd/C. The solution is then evaporated to yield the corresponding amine (>65% two steps).

D. General Procedure for the Coupling of Pyridoxal-5-Phosphate to Diazoarenes Method A:

1 mmol of an aminoarene is dissolved in 5 mL 2N HCl (with ethanol to help dissolution if necessary) and cooled to 0–5° C. in an ice/salt bath. 1 mmol of $NaNO_2$ is added portionwise and the diazonium salt is formed during 5 min. Then, 1 mmol (263 mg) of pyridoxal phosphate is dissolved in 10 mL of ice water with addition of 0.5 mL of saturated KOH. The diazonium salt is the added portionwise over a 1 min period and the resulting orange red solution left for 15 min. The solution is then warmed to RT for 1–4 h. The red solution is then cooled in an ice bath and 6N HCl is added dropwise forming a red precipitate. The precipitate is filtered off, washed with ice water and dried. The yield for this reaction ranged from 20 to 80%.

Method B:

1 mmol of an aminoaryl sulfonamide is dissolved in 2 mL 2N HCl (with 5 mL ethanol to help dissolution if necessary) and cooled to 0–5° C. in an ice/salt bath. 1 mmol of $NaNO_2$ is added portionwise and the diazonium salt is formed during 5 min. Then, 1 mmol (263 mg) of pyridoxal phosphate is dissolved in 2 mL of ice water with addition of 0.5 mL of saturated KOH. The diazonium salt is the added portionwise over a 1 min period and the resulting orange red solution left for 15 min. The solution is then warmed to RT for 14 h. The red solution is then cooled in an ice bath and diluted with ethanol until a yellow precipitate results. The precipitate is filtered and dried. The yield for this reaction ranged from 20 to 80%.

E. General Procedure for the Ethyl Acetal Formation

To a suspension of a pyridoxal derivative (5 mmol) in ethanol is added 200 μL of trimethylchlorosilane. The solution becomes orange as the product is formed. The solution is filtered and the supernatant is evacuated to yield the product as a foam (>90% yield).

F. General Procedure for the Oxime Formation

A pyridoxal derivative (0.1 mmol) is added to a 20% solution of hydroxylamine hydrochloride in 2–5 mL, pH 6 buffered water and stirred for 20 min. The pH is adjusted with hydrochloric acid until precipitation of the product is completed. The precipitate is filtered and dried (~65% yield).

DETAILED DESCRIPTION OF THE INVENTION EXAMPLES

Specific Examples for the Preparation of Derivatives of General Formula I

The following compounds were prepared from either from pyridoxal-5-phosphate using the procedures summarized in schemes 1, 2, 3 and 4.

Example 1

Preparation of 6-(3-Carboxy-2-methylphenylazo)-pyridoxal-5-phosphate

This product was obtained from commercially available 3-amino-2-methyl benzoic acid and pyridoxal-5-phosphate as described in general procedure D, method A. The final product was obtained in 85% yield.

$^1$H NMR (D$_2$O): δ 2.21 (s, 3H), 2.61 (s, 3H), 5.45 (s, 2H), 7.02 (t, J=6.5, 1H), 7.36 (d, J=6.0 1H), 7.52 (d, J=6.0, 1H), 10.06 (s, 1H). $^{31}$P NMR (D$_2$O): δ 6.88 (s).

Example 2

Preparation of 6-(4-Sulfamoylphenylazo)-pyridoxal-5-phosphate

This derivative was obtained from commercially available 4-aminobenzene sulfonamide and pyridoxal-5-phosphate as described in general procedure D, method A. The desired material was obtained in 79% yield.

$^1$H NMR (D$_2$O): δ 2.33 (s, 3H), 5.63 (s, 2H), 7.97 (d, J=8.0, 2H), 8.03 (d, J=8.1, 2H), 10.32 (s, 1H). $^{31}$P NMR (D$_2$O): δ 7.04 (s).

Example 3

Preparation of 6-[4-(N-(1-Adamantyl)sulfamoyl)phenylazo]-pyridoxal-5-phosphate Hydrochloride Step A. Preparation of N-Adamantan-1-yl-4-aminobenzenesulfonamide The coupling of amino adamantane with p-acetamidobenzenesulfonyl chloride was achieved using general procedure B (steps 1 and 2). The title product was used as such without further purification at the next step.

Step B. Preparation of 6-[4-(N-(1-Adamantyl)sulfamoyl)phenylazo]-pyridoxal-5-phosphate Hydrochloride The title compound was prepared from N-adamantan-1-yl-4-aminobenzenesulfonamide (step A) and pyridoxal-5-phosphate as described in general procedure D, method A. The final product was obtained in 84% yield.

$^1$H NM (D$_2$O): δ 1.45 (s, 6H), 1.66 (s, 6H), 1.88 (s, 3H), 2.33 (s, 3H), 5.63 (s, 2H), 7.97 (d, J=8.0, 2H), 8.03 (d, J=8.1, 2H), 10.32 (s, 1H). $^{31}$P NMR (D$_2$O): δ 7.00 (s).

Example 4

Preparation of 6-[3-(N-(1-Adamantyl)carbamoyl)phenylazo]-pyridoxal-5-phosphate Hydrochloride Step A. Preparation of N-Adamantan-1-yl-3-aminobenzenecarboxamide The coupling of amino adamantane with m-nitrobenzoyl chloride was achieved using general procedure A (steps 1 and 2). The title product was used as such without further purification at the next step.

Step B. Preparation of 6-[3-(N-(1-Adamantyl)carbamoyl)phenylazo]-pyridoxal-5-phosphate Hydrochloride This compound was prepared from N-adamantan-1-yl-4-aminobenzenecarboxamide (step A) and pyridoxal-5-phosphate as described in general procedure D, method A. The final product was obtained in 93% yield.

$^1$H NMR (D$_2$O): δ 1.45 (s, 6H), 1.66 (s, 6H), 1.88 (s, 3H), 2.33 (s, 3H), 5.63 (s, 2H), 7.45 (t, J=8.0, 1H), 7.72 (d, J=7.0, 1H), 7.99 (t, J=8.1, 1H), 8.11 (s, 1H), 10.32 (s, 1H). $^{31}$P NMR (D$_2$O): δ 7.00 (s).

Example 5

Preparation of 6-[4-(N-(2-E-Caprolactamyl)-N-isobutylsulfamoyl)phenylazo]-pyridoxal-5-phosphate Hydrochloride Step A. Preparation of L-Lysine Methyl Ester Dihydrochloride MeOH (J. Org. Chem. 44, 4841 (1979))

To a stirred suspension of L-lysine monohydrochloride (190.7 g, 1.08 mol) in MeOH (3 L) was added (via a cannula) trimethylsilylchloride (350 mL). The mixture quickly became clear and homogeneous. The solution was stirred at reflux for 3 h and then at room temperature for 2 h. The reaction flask was left overnight in a refrigerator cooled to −75° C. The large crystals obtained were filtered, washed with cold MeOH (100 mL) and dried in vacuo for 24 h at room temperature. L-lysine methyl ester dihydrochloride MeOH (275.8 g) was obtained in 99.4% yield.

$^1$H NMR (DMSO-d$_6$): δ 1.36 (m, 1H), 1.45 (m, 1H), 1.58 (m, 2H), 1.81 (m, 2H), 2.74 (br s, 2H), 3.11 (s, 3H), 3.72 (s, 3H), 3.94 (t, J=4.0, 1H), 8.12 (br s, 3H), 8.72 (br s, 3H).

Step B. Preparation of L-α-Amino-ε-caprolactam Hydrochloride (or (3S)-3-Amino-azepan-2-one Hydrochloride) (J. Org. Chem. 44, 4841 (1979))

Sodium methylate 58.73 g (1 mole) was dissolved in cold MeOH (1 L). About one half of this solution was cannulated into a solution of L-lysine methyl ester dihydrochloride MeOH (132.5 g, 0.5 mole) in 1 L MeOH. The suspension was allowed to warm and dissolved. The remainder sodium methylate was added with concurrent apparition of NaCl. The mixture was then allowed to reflux for 4 h, after which 5 g of NHCl was added. The solution then sat at RT for 18 h and was filtered through celite. Evaporation of the MeOH resulted in a thick opaque syrup. The excess NaCl was removed by redissolving the mixture in boiling glyme (100 mL, 2x), filtering through celite and evaporating in vacuo. The resulting clear oil was taken up in ethanol and acidified with 1N HCl. Cooling gave a mass of fine white needles which were filtered and dried in vacuo to yield 69.71 g, 85% of the title compound. mp: 301–306° C.

LC-MS: 129.1 (M+H)$^+$, 99% pure. [α]$_D^{20}$=−24.8 (c=3.4, 1N HCl). $^1$H NMR (DMSO-d$_6$): δ 1.17 (q, J=12.6, 1H), 1.45 (q, J=12.6, 1H), 1.58 (q, J=12.6, 1H), 1.71 (d, J=12.6, 1H), 1.86 (d, J=12.6, 1H), 1.94 (d, J=12.6, 1H), 3.03 (m, 1H), 3.15 (m, 1H), 4.03 (d, J=12.6, 1H), 8.12 (br s, 1H), 8.22 (br s, 3H). $^{13}$C NMR (DMSO-d$_6$): δ 28.2, 29.7, 29.9, 41.6, 53.4, 173.2.

Step C. Preparation of Nα-Isobutyl-L-α-amino-ε-caprolactam (or (3S)-3-Isobutylamino-azepan-2-one)

L-α-amino-ε-caprolactam (60.0 g, 0.47 mol) was dissolved in dichloroethane (DCE, 100 mL) containing isobutyraldehyde (37.0 g, 0.5 mole) and stirred until the heat evolved was dissipated. Then, DCE (2 L) and AcOH (35 mL) were added to the solution followed by 0.5 mole of powdered NaBH(OAc)$_3$. The slightly turbid mixture was stirred at 60° C. for 2 h, and at room temperature for 12 h. The solution was treated with 1M K$_2$CO$_3$ (1 L) and stirred for a further 2 h. The DCE layer was dried with MgSO$_4$, filtered and evaporated. The oil thus obtained crystallizes slowly on standing (87 g, 94.5%) and was used without further purification in the next step. mp: 52–54° C. A small sample was converted to the hydrochloride salt by adding the solid to a solution of 1N HCl in 95% EtOH.

$^1$H NMR (CDCl$_3$): δ 0.93 (d, J=6.5, 3H), 0.97 (d, J=6.5, 3H), 1.39 (t, J=9.8, 1H), 1.47 (m, 1H), 1.78–1.65 (m, 2H), 2.00–1.93 (m, 2H), 2.32–2.2 (m, 2H), 2.38 (t, J=9.7, 1H), 3.16 (m, 3H), 6.62 (s, 1H (NH)).

Step D. Preparation of 4-Amino-N-isobutyl-N-(2-oxo-azepan-3-yl)-benzenesulfonamide The coupling of Nα-isobutyl-L-α-amino-ε-caprolactam (step C) with p-acetamidobenzenesulfonyl chloride was achieved using general procedure B (steps 1 and 2). The title product was used as such without further purification at the next step.

Step E. Preparation of 6-[4-(N-(2-F-Caprolactamyl)-N-isobutylsulfamoyl)phenylazo]-pyridoxal-5-phosphate Hydrochloride The title compound was prepared from 4-amino-N-isobutyl-N-(2-oxo-azepan-3-yl)-benzenesulfonamide (step D) and pyridoxal-5-phosphate as described in general procedure D, method A. The final product was obtained in 87% yield.

$^1$H NMR (D$_2$O): δ 10.32 (s, 1H), 8.03 (d, J=8.1, 2H), 7.97 (d, J=8.0, 2H), 5.63 (s, 2H), 5.7 (s, 1H (NH)), 4.48 (d, J=10.6, 1H), 3.21–3.26 (m, 1H), 3.10–3.06 (m, 2H), 2.97 2.98 (m, 1H), 2.86–2.89 (m, 1H), 2.33 (s, 3H), 1.96–1.99 (m, 1H), 1.84–1.87 (m, 1H), 1.56–1.73 (m, 4H), 1.12 (q, J=8.3, 1H), 0.80 (d, J=6.2, 3H), 0.74 (d, J=6.2, 3H). $^{31}$P NMR (D$_2$O): δ 6.96 (s).

Example 6

Preparation of 6-[3-(1-Piperidinesulfonyl) phenylazo]-pyridoxal-5-phosphate

Step A. Preparation of 3-(Piperidine-1-sulfonyl)-phenylamine

The coupling of piperidine with m-nitrobenzenesulfonyl chloride was achieved using general procedure C (steps 1 and 2). The title product was used as such without further purification at the next step.

Step B. Preparation of 6-[3-(1-Piperidinesulfonyl) phenylazo]-pyridoxal-5-phosphate The title material was prepared from 3-(piperidine-1-sulfonyl)-phenylamine (step A) and pyridoxal-5-phosphate as described in general procedure D, method A. The final product was obtained in 88% yield.

$^1$H NMR (D$_2$O): δ 1.45 (s, 2H), 1.66 (s, 4H), 1.88 (s, 3H), 2.33 (s, 3H), 3.00 (s, 4H), 5.63 (s, 2H), 7.67 (t, J=8.0, 1H), 7.72 (d, J=7.0, 1H), 8.05 (t, J=8.1, 2H), 10.32 (s, 1H). $^{31}$P NMR (D$_2$O): δ 7.03 (s).

Example 7

Preparation of 6-[4-(1-Piperidinesulfonyl) phenylazo]-pyridoxal-5-phosphate

Step A. Preparation of 4-(Piperidine-1-sulfonyl)-phenylamine

The coupling of piperidine with p-acetamidobenzenesulfonyl chloride was achieved using general procedure B (steps 1 and 2). The title product was used as such without further purification at the next step.

Step B. Preparation of 6-[4-(1-Piperidinesulfonyl) phenylazo]-pyridoxal-5-phosphate This derivative was prepared from 4-(piperidine-1-sulfonyl)-phenylamine (step A) and pyridoxal-5-phosphate as described in general procedure D, method A. The final product was obtained in 56% yield.

$^1$H NMR (D$_2$O): δ 1.45 (s, 2H), 1.66 (s, 4H), 1.88 (s, 3H), 2.33 (s, 3H), 3.00 (s, 4H), 5.63 (s, 2H), 7.97 (d, J=8.0, 2H), 8.03 (d, J=8.1, 2H), 10.32 (s, 1H). $^{31}$P NMR (D$_2$O): δ 7.02 (s).

Example 8

Preparation of 6-[3-(1-Piperidinecarbonyl) phenylazo]-pyridoxal-5-phosphate

Step A. Preparation of (3-Aminophenyl)-piperidin-1-yl-methanone

The coupling of piperidine with m-nitrobenzoyl chloride was achieved using general procedure A (steps 1 and 2). The title product was used as such without further purification at the next step.

Step B. Preparation of 6-[3-(1-Piperidinecarbonyl) phenylazo]-pyridoxal-5-phosphate This compound was prepared from (3-aminophenyl)-piperidin-1-yl-methanone (step A) and pyridoxal-5-phosphate as described in general procedure D, method A. The final product was obtained in 16% yield.

$^1$H NMR (D$_2$O): δ 2.26 (s, 3H), 3.28 (s, 3H), 3.56 (s, 3H), 5.50 (s, 2H), 7.24 (d, J=7.1, 1H), 7.47 (t, J=7.1, 1H), 7.78 (s, 1H), 7.91 (d, J=7.2, 1H), 10.23 (s, 1H). $^{31}$P NMR (D$_2$O): δ 7.00 (s).

Example 9

Preparation of 6-[3-(tert-Butylsulfamoyl) phenylazo]-pyridoxal-5-phosphate

Step A. Preparation of 3-Amino-N-tert-butyl-benzenesulfonamide

The coupling of tert-butyl amine with m-nitrobenzenesulfonyl chloride was achieved using general procedure C (steps 1 and 2). The title product was used as such without further purification at the next step.

Step B. Preparation of 6-[3-(tert-Butylsulfamoyl) phenylazo]-pyridoxal-5-phosphate The title material was prepared from 3-amino-N-tert-butyl-benzenesulfonamide (step A) and pyridoxal-5-phosphate as described in general procedure D, method A. The final product was obtained in 75% yield.

$^1$H NMR (D$_2$O): δ 1.00 (5, 9H), 2.33 (s, 3H), 5.63 (s, 2H), 7.45 (t, J=8.0, 1H), 7.72 (d, J=7.0, 1H), 7.99 (t, J=8.1, 1H), 8.11 (s, 1H), 10.32 (s, 1H). $^{31}$P NMR (D$_2$O): δ 7.02 (s).

Example 10

Preparation of 6-[4-(tert-Butylsulfamoyl) phenylazo]-pyridoxal-5-phosphate

Step A. Preparation of 4-Amino-N-tert-butyl-benzenesulfonamide

The coupling of tert-butyl amine with p-acetamidobenzenesulfonyl chloride was achieved using general procedure B (steps 1 and 2). The title product was used as such without further purification at the next step.

Step B. Preparation of 6-[4-(tert-Butylsulfamoyl) phenylazo]-pyridoxal-5-phosphate The title material was prepared from 4-amino-N-tert-butyl-benzenesulfonamide (step A) and pyridoxal-5-phosphate as described in general procedure D, method A. The final product was obtained in 82% yield.

$^1$H NMR (D$_2$O): δ 1.00 (s, 9H), 2.33 (s, 3H), 5.63 (s, 2H), 7.72 (d, J=7.0, 2H), 7.99 (d, J=8.1, 2H), 10.32 (s, 1H). $^{31}$P NMR (D$_2$O): δ 7.04 (s).

Example 11

Preparation of 6-[4-(tert-Butylcarbamoyl) phenylazo]-pyridoxal-5-phosphate

Step A. Preparation of 4-Amino-N-tert-butyl-benzamide

The coupling of tert-butyl amine with p-nitrobenzoyl chloride was achieved using general procedure A (steps 1 and 2). The title product was used as such without further purification at the next step.

Step B. Preparation of 6-[4-(tert-Butylcarbamoyl) phenylazo]-pyridoxal-5-phosphate This compound was prepared from 4-amino-N-tert-butyl-benzamide (step A) and pyridoxal-5-phosphate as described in general procedure D, method A. The final product was obtained in 23% yield.

$^1$H NMR (D$_2$O): δ 1.00 (s, 9H), 2.33 (s, 3H), 5.63 (s, 2H), 7.15 (t, J=8.0, 1H), 7.72 (d, J=7.0, 1H), 7.89 (t, J=8.1, 1H), 8.01 (s, 1H), 10.32 (s, 1H). $^{31}$P NMR (D$_2$O): δ 7.00 (s).

Example 12

Preparation of 6-[3-(1-Pyrrolinesulfonyl) phenylazo]-pyridoxal-5-phosphate

Step A. Preparation of 3-(Pyrrolinine-1-sulfonyl)-phenylamine

The coupling of pyrrolidine with m-nitrobenzenesulfonyl chloride was achieved using general procedure C (steps 1 and 2). The title product was used as such without further purification at the next step.

Step B. Preparation of 6-[3-(1-Pyrrolinesulfonyl)phenylazo] pyridoxal-5-phosphate The title material was prepared from 3-(pyrrolinine-1-sulfonyl)-phenylamine (step A) and pyridoxal-5-phosphate as described in general procedure D, method A. The final product was obtained in 18% yield.

$^1$H NMR (D$_2$O): δ 1.56 (s, 4H), 2.33 (s, 3H), 3.00 (s, 4H), 5.63 (s, 2H), 7.67 (t, J=8.0 1H), 7.72 (d, J=7.0, 1H), 8.05 (t, J=8.1, 2H), 10.32 (s, 1H). $^{31}$P NMR (D$_2$O): δ 7.00 (s).

Example 13

Preparation of 6-[3-(Isobutylcarbamoyl)phenylazo]-pyridoxal-5-phosphate

Step A. Preparation of 3-Amino-N-isobutyl-benzamide

The coupling of isobutylamine with m-nitrobenzoyl chloride was achieved using general procedure A (steps 1 and 2). The title product was used as such without further purification at the next step.

Step B. Preparation of 6-[3-(Isobutylcarbamoyl)phenylazo]-pyridoxal-5-phosphate

The compound was prepared from 3-amino-N-isobutyl-benzamide (step A) and pyridoxal-5-phosphate as described in general procedure D, method A. The final product was obtained in 14% yield.

$^1$H NMR (D$_2$O): δ 0.69 (m, 6H), 1.49 (m, 1H), 2.30 (s, 3H), 2.49 (d, J=6.2, 2H), 5.55 (s, 2H), 7.33 (t, J=7.4, 1H), 7.54 (d, J=7.0, 1H), 7.65 (d, J=7.0, 1H), 7.98 (s, 1H), 10.26 (s, 1H). $^{31}$P NMR (D$_2$O): δ 7.00 (s).

Example 14

Preparation of 6-[4-(Cyclohexylcarbamoyl) phenylazo]-pyridoxal-5-phosphate

Step A. Preparation of 4-Amino-N-cyclohexyl-benzamide

The coupling of cyclohexyl amine with p-nitrobenzoyl chloride was achieved using general procedure A (steps 1 and 2). The title product was used as such without further purification at the next step.

Step B. Preparation of 6-[4-(Cyclohexylcarbamoyl) phenylazo]-pyridoxal-5-phosphate This compound was prepared from 4-amino-N-cyclohexyl-benzamide (step A) and pyridoxal-5-phosphate as described in general procedure D, method A. The final product was obtained in 48% yield.

$^1$H NMR (D$_2$O): δ 1.04 (m, 5H), 1.41 (d, J=11.0, 1H), 1.54 (d, J=18.3, 4H), 2.31 (s, 3H), 2.70 (m, 1H), 5.58 (s, 2H), 7.6 (d, J=7.0, 2H), 7.73 (d, J=7.2, 2H), 10.27 (s, 1H). $^{31}$P NMR (D$_2$O): δ 7.03 (s).

Example 15

Preparation of 6-[4-(1-Pyrrolinesulfonyl) phenylazo]-pyridoxal-5-phosphate

Step A. Preparation of 4-(Pyrrolinine-1-sulfonyl)-phenylamine

The coupling of pyrrolidine with p-acetamidobenzenesulfonyl chloride was achieved using general procedure B (steps 1 and 2). The title product was used as such without further purification at the next step.

Step B. Preparation of 6-[4-(1-Pyrrolinesulfonyl) phenylazo]-pyridoxal-5-phosphate The title material was prepared from 4-(pyrrolinine-1-sulfonyl)-phenylamine (step A) and pyridoxal-5-phosphate as described in general procedure D, method A. The final product was obtained in 21% yield.

$^1$H NMR (D$_2$O): δ 1.65 (s, 4H), 2.31 (s, 3H), 3.21 (s, 4H), 5.55 (s, 2H), 7.91 (d, J=8.6, 2H), 8.02 (d, J=8.4, 2H), 10.27 (s, 1H). $^{31}$P NMR (D$_2$O): δ 7.03 (s).

Example 16

Preparation of 6-[3-(Isobutylsulfamoyl)phenylazo]-pyridoxal-5-phosphate

Step A. Preparation of 3-Amino-N-isobutyl-benzenesulfonamide

The coupling of isobutyl amine with in-nitrobenzenesulfonyl chloride was achieved using general procedure C (steps 1 and 2). The title product was used as such without further purification at the next step.

Step B. Preparation of 6-[3-(Isobutylsulfamoyl)phenylazo]-pyridoxal-5-phosphate

The title material was prepared from 3-amino-N-isobutyl-benzenesulfonamide (step A) and pyridoxal-5-phosphate as described in general procedure D, method A. The final product was obtained in 24% yield.

$^1$H NMR (D$_2$O): δ 0.69 (m, 6H), 1.49 (m, 1H), 2.30 (s, 3H), 2.49 (d, J=6.2, 2H), 5.55 (s, 2H), 7.57 (t, J=7.7, 1H), 7.72 (d, J=7.6, 1H), 7.96 (d, J=8.0, 1H), 8.13 (s, 1H), 10.26 (s, 1H). $^{31}$P NMR (D$_2$O): δ 7.02 (s).

Example 17

Preparation of 6-[4-(Isobutylsulfamoyl)phenylazo] pyridoxal-5-phosphate

Step A. Preparation of 4-Amino-N-isobutyl-benzenesulfonamide

The coupling of isobutyl amine with p-acetamidobenzenesulfonyl chloride was achieved using general procedure B (steps 1 and 2). The title product was used as such without further purification at the next step.

Step B. Preparation of 6-[4-(Isobutylsulfamoyl)phenylazo]-pyridoxal-5-phosphate

The title material was prepared from 4-amino-N-isobutyl-benzenesulfonamide (step A) and pyridoxal-5-phosphate as described in general procedure D, method A. The final product was obtained in 27% yield.

$^1$H NMR (D$_2$O): δ 0.67 (m, 6H), 1.46 (m, 1H), 2.27 (s, 3H), 2.46 (d, J=7.0, 2H), 5.51 (s, 2H), 7.76 (d, J=8.6, 2H), 7.90 (d, J=8.4, 2H), 10.24 (s, 1H). $^{31}$P NMR (D$_2$O): δ 7.05 (s).

Example 18

Preparation of 6-[4-(Cyclohexylsulfamoyl) phenylazo]-pyridoxal-5-phosphate

Step A. Preparation of 4-Amino-N-cyclohexyl-benzenesulfonamide

The coupling of cyclohexyl amine with p-acetamidobenzenesulfonyl chloride was achieved using general procedure B (steps 1 and 2). The title product was used as such without further purification at the next step.

Step B. Preparation of 6-[4-(Cyclohexylsulfamoyl) phenylazo]pyridoxal-5-phosphate The title material was prepared from 4-amino-N-cyclohexyl-benzenesulfonamide (step A) and pyridoxal-5-phosphate as described in general procedure D, method A. The final product was obtained in 25% yield.

$^1$H NMR (D$_2$O): δ 1.04 (m, 5H), 1.41 (d, J=11.0, 1H), 1.54 (d, J=18.3, 4H), 2.31 (s, 3H), 2.69 (m, 1H), 5.56 (s, 2H), 7.83 (d, J=8.0, 2H), 7.93 (d, J=8.2, 2H), 10.27 (s, 1H). $^{31}$P NMR (D$_2$O): δ 7.05 (s).

Example 19

Preparation of 6-[3-(Butylsulfamoyl)phenylazo]-pyridoxal-5-phosphate

Step A. Preparation of 3-Amino-N-butyl-benzenesulfonamide

The coupling of butyl amine with m-nitrobenzenesulfonyl chloride was achieved using general procedure C (steps 1 and 2). The title product was used as such without further purification at the next step.

Step B. Preparation of 6-[3-(Butylsulfamoyl)phenylazo]-pyridoxal-5-phosphate

This derivative was prepared from 3-amino-N-butyl-benzenesulfonamide (step A) and pyridoxal-5-phosphate as described in general procedure D, method A. The final product was obtained in 54% yield.

$^1$H NMR (D$_2$O): δ 0.85 (t, J=7.4, 3H), 1.31 (quint, J=7.4, 2H), 1.54 (quint, J=7.3, 2H), 2.31 (s, 3H), 3.34 (t, J=7.1, 2H), 5.55 (s, 2H), 7.58 (t, J=8.0, 1H), 7.74 (d, J=7.4, 1H), 8.02 (d, J=8.1, 1H), 8.14 (s, 1H), 10.28 (s, 1H). $^{31}$P NMR (D$_2$O): δ 7.04 (s).

Example 20

Preparation of 6-[4-(Methylsulfamoyl)phenylazo]-pyridoxal-5-phosphate

Step A. Preparation of 4-Amino-N-methyl-benzenesulfonamide

The coupling of methyl amine with p-acetamidobenzenesulfonyl chloride was achieved using general procedure B (steps 1 and 2). The title product was used as such without further purification at the next step.

Step B. Preparation of 6-[4-(Methylsulfamoyl)phenylazo]-pyridoxal-5-phosphate

The title material was prepared from 4-amino-N-methyl-benzenesulfonamide (step A) and pyridoxal-5-phosphate as described in general procedure D, method A. The final product was obtained in 29% yield.

$^1$H NMR (D$_2$O): δ 2.30 (s, 3H), 2.83 (s, 3H), 5.51 (s, 2H), 7.76 (d, J=8.1, 2H), 7.86 (d, J=7.6, 2H), 10.26 (s, 1H). $^{31}$P NMR (D$_2$O): δ 7.05 (s).

Example 21

Preparation of 6-[3-(2-Hydroxyethylsulfamoyl) phenylazo]-pyridoxal-5-phosphate Step A. Preparation of 3-Amino-N-(2-hydroxyethyl)-benzenesulfonamide The coupling of ethanol amine with m-nitrobenzenesulfonyl chloride was achieved using general procedure C (steps 1 and 2). The title product was used as such without further purification at the next step.

Step B. Preparation of 6-[3-(2-Hydroxyethylsulfamoyl) phenylazo]-pyridoxal-5-phosphate The title material was prepared from 3-amino-N-(2-hydroxyethyl)-benzenesulfonamide (step A) and pyridoxal-5-phosphate as described in general procedure D, method A. The final product was obtained in 21% yield.

$^1$H NMR (D$_2$O): δ 2.30 (s, 3H), 3.88 (br s, 2H), 5.51 (s, 2H), 7.46 (s, 1H), 7.66 (s, 1H), 8.00 (s, 1H), 8.17 (s, 1H), 10.26 (s, 1H). $^{31}$P NMR (D$_2$O): δ 6.99 (s).

Example 22

Preparation of 6-(3,5-Dicarboxyphenylazo)-pyridoxal-5-phosphate

This product was obtained from commercially available 5-amino-isophthalic acid and pyridoxal-5-phosphate as described in general procedure D, method A. The desired material was obtained in 70% yield.

$^1$H NMR (D$_2$O): δ 2.30 (s, 3H), 5.65 (s, 2H), 8.21 (s, 1H), 8.32 (s, 2H), 10.26 (s, 1H). $^{31}$P NMR (D$_2$O): δ 7.02 (s).

Example 23

Preparation of 6-[4-(2,6-Dimethyl-4-pyrimidinyl) sulfamoyl)phenylazo]-pyridoxal-5-phosphate Step A. Preparation of 4-Amino-N-(2,6-dimethyl-pyrimidin-4-yl)-benzenesulfonamide The coupling of 2,6-dimethyl-pyrimidin-4-ylamine with p-acetamidobenzenesulfonyl chloride was achieved using general procedure B (steps 1 and 2). The title product was used as such without further purification at the next step.

Step B. Preparation of 6-[4-(2,6-Dimethyl-4-pyrimidinyl) sulfamoyl)phenylazo]-pyridoxal-5-phosphate The title material was prepared from 4-amino-N-(2,6-dimethyl-pyrimidin-4-yl)-benzenesulfonamide (step A) and pyridoxal-5-phosphate as described in general procedure D, method B. The final product was obtained in 42% yield.

$^1$H NMR (D$_2$O): δ 1.90 (s, 3H), 2.10 (s, 3H), 2.30 (s, 3H), 5.65 (s, 2H), 6.28 (s, 1H), 7.87 (s, 4H), 10.16 (s, 1H). $^{31}$P NMR (D$_2$O): δ 6.96 (s).

Example 24

Preparation of 6-[4-(2-Thiazolylsulfamoyl) phenylazo]-pyridoxal-5-phosphate

Step A. Preparation 4-Amino-N-thiazol-2-yl-benzenesulfonamide

The coupling of thiazol-2-ylamine with p-acetamidobenzenesulfonyl chloride was achieved using general procedure B (steps 1 and 2). The title product was used as such without further purification at the next step.

Step B. Preparation 6-[4-(2-Thiazolylsulfamoyl) phenylazo]-pyridoxal-5-phosphate The title material was prepared from 4-amino-N-thiazol-2-yl-benzenesulfonamide (step A) and pyridoxal-5-phosphate as described in general procedure D, method A. The final product was obtained in 29% yield.

$^1$H NMR (D$_2$O): δ 2.31 (s, 3H), 5.55 (s, 2H), 6.46 (s, 1H), 6.97 (s, 1H), 7.88 (s, 4H), 10.26 (s, 1H). $^{31}$P NMR (D$_2$O): δ 7.02 (s).

Example 25

Preparation of 6-[4-(2-Pyrimidylsulfamoyl)phenylazo]-pyridoxal-5-phosphate

Step A. Preparation of 4-Amino-N-pyrimidin-2-yl-benzenesulfonamide

The coupling of pyrimidin-2-ylamine with p-acetamidobenzenesulfonyl chloride was achieved using general procedure B (steps 1 and 2). The title product was used as such without further purification at the next step.

Step B. Preparation of 6-[4-(2-Pyrimidylsulfamoyl)phenylazo]pyridoxal-5-phosphate The title material was prepared from 4-amino-N-pyrimidin-2-yl-benzenesulfonamide (step A) and pyridoxal-5-phosphate as described in general procedure D, method A. The final product was obtained in 17% yield.

$^1$H NMR (D$_2$O): δ 2.30 (s, 3H), 5.65 (s, 2H), 6.76–6.88 (m, 3H), 7.77 (s, 4H), 10.06 (s, 1H). $^{31}$P NMR (D$_2$O): δ 6.88 (s).

Example 26

Preparation of 6-[3-(Methylsulfamoyl)phenylazo]-pyridoxal-5-phosphate

Step A. Preparation of 3-Amino-N-methyl-benzenesulfonamide

The coupling of methyl amine with m-nitrobenzenesulfonyl chloride was achieved using general procedure C (steps 1 and 2). The title product was used as such without further purification at the next step.

Step B. Preparation of 6-[3-(Methylsulfamoyl)phenylazo]-pyridoxal-5-phosphate

The title material was prepared from 3-amino-N-methyl-benzenesulfonamide (step A) and pyridoxal-5-phosphate as described in general procedure D, method A. The final product was obtained in 2% yield.

$^1$H NMR (D$_2$O): δ 2.29 (s, 3H), 2.86 (s, 3H), 5.52 (s, 2H), 7.55 (t, J=7.2, 1H), 7.73 (d, J=7.5, 1H), 7.98 (d, J=7.7, 1H), 8.13 (s, 1H), 10.25 (s, 1H). $^{31}$P NMR (D$_2$O): δ 7.05 (s).

Example 27

Preparation of 6-[3-(Morpholinesulfamoyl)phenylazo]-pyridoxal-5-phosphate

Step A. Preparation of 3-(Morpholine-4-sulfonyl)-phenylamine

The coupling of morpholine with m-nitrobenzenesulfonyl chloride was achieved using general procedure C (steps 1 and 2). The title product was used as such without further purification at the next step.

Step B. Preparation of 6-[3-(Morpholinesulfamoyl)phenylazo]-pyridoxal-5-phosphate The title material was prepared from 3-(morpholine-4-sulfonyl)-phenylamine (step A) and pyridoxal-5-phosphate as described in general procedure D, method A. The final product was obtained in 2% yield.

$^1$H NMR (D$_2$O): δ 2.30 (s, 3H), 3.04 (s, 4H), 3.70 (s, 4H), 5.55 (s, 2H), 7.73 (t, J=7.8, 1H), 7.78 (d, J=7.5, 1H), 8.12 (s, 1H), 8.17 (d, J=8.3, 1H), 10.27 (s, 1H). $^{31}$P NMR (D$_2$O): δ 7.05 (s).

Example 28

Preparation of 6-[3-(3-Pyridylcarbamoyl)phenylazo]-pyridoxal-5-phosphate

Step A. Preparation of 3-Amino-N-pyridin-3-yl-benzamide

The coupling of 3-aminopyridine with m-nitrobenzoyl chloride was achieved using general procedure A (steps 1 and 2). The title product was used as such without further purification at the next step.

Step B. Preparation of 6-[3-(3-Pyridylcarbamoyl)phenylazo]-pyridoxal-5-phosphate The compound was prepared from 3-amino-N-pyridin-3-yl-benzamide (step A) and pyridoxal-5-phosphate as described in general procedure D, method A. The final product was obtained in 42% yield.

$^1$H NMR (D$_2$O): δ 2.31 (s, 3H), 5.55 (s, 2H), 7.30 (t, J=6.5 Hz, 1H), 7.53 (m, 2H), 7.91 (d, J=8.1, 1H), 7.96 (d, J=7.9, 1H), 8.07 (d, J=6.6, 1H), 8.22 (s, 1H), 8.34 (s, 1H), 10.26 (s, 1H). $^{31}$P NMR (D$_2$O): δ 7.03 (s).

Example 29

Preparation of 6-[3-(2-Pyridylcarbamoyl)phenylazo]-pyridoxal-5-phosphate

Step A. Preparation of 3-Amino-N-pyridin-2-yl-benzamide

The coupling of 2-aminopyridine with m-nitrobenzoyl chloride was achieved using general procedure A (steps 1 and 2). The title product was used as such without further purification at the next step.

Step B. Preparation of 6-[3-(2-Pyridylcarbamoyl)phenylazo]-pyridoxal-5-phosphate This compound was prepared from 3-amino-N-pyridin-2-yl-benzamide (step A) and pyridoxal-5-phosphate as described in general procedure D, method A. The final product was obtained in 28% yield.

$^1$H NMR (D$_2$O): δ 2.31 (s, 3H), 5.56 (s, 2H), 6.97 (m, 1H), 7.53 (m, 2H), 7.67 (t, J=7.5, 1H), 7.87 (d, J=7.5, 1H), 7.95 (m, 2H), 8.26 (s, 1H), 10.27 (s, 1H). $^{31}$P NMR (D$_2$O): δ 7.03 (s).

Example 30

Preparation of 6-[3-(4-Pyridylcarbamoyl)phenylazo]-pyridoxal-5-phosphate

Step A. Preparation of 3-Amino-N-pyridin-4-yl-benzamide

The coupling of 4-aminopyridine with m-nitrobenzoyl chloride was achieved using general procedure A (steps 1 and 2). The title product was used as such without further purification at the next step.

Step B. Preparation of 6-[3-(4-Pyridylcarbamoyl)phenylazo]-pyridoxal-5-phosphate This compound was prepared from 3-amino-N-pyridin-4-yl-benzamide (step A) and pyridoxal-5-phosphate as described in general procedure D, method A. The final product was obtained in 28% yield.

$^1$H NMR (D$_2$O): δ 2.32 (s, 3H), 5.56 (s, 2H), 7.12 (d, J=7.0, 2H), 7.54 (t, J=7.5, 1H), 7.89 (d, J=7.8, 1H), 7.95 (d, J=7.9, 1H), 8.24 (d, J=7.2, 2H), 8.33 (s, 1H), 10.26 (s, 1H). $^{31}$P NMR (D$_2$O): δ 7.03 (s).

Example 31

Preparation of 6-[3-(5-Isoquinolylcarbamoyl)phenylazo]-pyridoxal-5-phosphate

Step A. Preparation of 3-Amino-N-isoquinolin-5-yl-benzamide

The coupling of isoquinolin-5-ylamine with m-nitrobenzoyl chloride was achieved using general procedure A (steps 1 and 2). The title product was used as such without further purification at the next step.

Step B. Preparation of 6-[3-(5-Isoquinolylcarbamoyl) phenylazo]-pyridoxal-5-phosphate This derivative was prepared from 3-amino-N-isoquinolin-5-yl-benzamide (step A) and pyridoxal-5-phosphate as described in general procedure D, method A. The final product was obtained in 53% yield.

$^1$H NMR (D$_2$O): δ 2.31 (s, 3H), 5.55 (s, 2H), 7.32 (d, J=7.7, 1H), 7.57 (d, J=8.0, 2H), 7.75 (d, J=7.8, 2H), 7.98 (d, J=7.5, 1H), 8.04 (d, J=7.2, 1H), 8.23 (d, J=7.1, 1H), 8.42 (s, 1H), 9.10 (s, 1H), 10.26 (s, 1H). $^{31}$P NMR (D$_2$O): δ 7.05 (s).

Example 32

Preparation of 6-[4-(3-Isoazolylsulfamoyl) phenylazo]-pyridoxal-5-phosphate

Step A. Preparation of 4-Amino-N-isoxazol-3-yl-benzenesulfonamide

The coupling of amino isooxazole with p-acetamidobenzenesulfonyl chloride was achieved using general procedure B (steps 1 and 2). The title product was used as such without further purification at the next step.

Step B. Preparation of 6-[4-(3-Isoazolylsulfamoyl) phenylazo]-pyridoxal-5-phosphate The title material was prepared from 4-amino-N-isoxazol-3-yl-benzenesulfonamide (step A) and pyridoxal-5-phosphate as described in general procedure D, method A. The final product was obtained in 40% yield.

$^1$H NMR (D$_2$O): δ 2.33 (s, 3H), 5.63 (s, 2H), 6.42 (s, 1H), 7.97 (d, J=8.0, 2H), 8.03 (d, J=8.1, 2H), 8.65 (s, 1H), 10.32 (s, 1H). $^{31}$P NMR (D$_2$O): δ 7.06 (s).

Example 33

Preparation of 6-(2-Nitrophenylazo)-pyridoxal-5-phosphate

This product was obtained from commercially available 2-nitrophenylamine and pyridoxal-5-phosphate as described in general procedure D, method A. The desired material was obtained in 27% yield.

$^1$H NMR (D$_2$O): δ 2.30 (s, 3H), 5.46 (s, 2H), 7.44 (t, J=6.7, 1H), 7.67–7.71 (m, 2H), 7.82 (t, J=6.5, 1H), 10.22 (s, 1H). $^{31}$P NMR (D$_2$O): δ 7.04 (s).

Example 34

Preparation of 6-(3-Chlorophenylazo)-pyridoxal-5-phosphate

This product was obtained from commercially available 3-chlorophenylamine and pyridoxal-5-phosphate as described in general procedure D, method A. The desired material was obtained in 58% yield.

$^1$H NMR (D$_2$O): δ 2.30 (s, 3H), 5.46 (s, 2H), 7.24–7–36 (m, 1H), 7.67 (t, J=5.5, 2H), 7.82 (s, 1H), 10.12 (s, 1H). $^{31}$P NMR (D$_2$O): δ 7.04 (s).

Example 35

Preparation of 6-(3-Sulfamoylphenylazo)-pyridoxal-5-phosphate

Step A. Preparation of 3-Aminobenzene Sulfonamide

To a solution of 3-nitrobenzene sulfonamide (5 mmol) dissolved in argon (Ar) saturated MeOH was suspended 200 mg of 10% Pd/C. A balloon of H$_2$ gas was connected via a needle to the reaction mixture which was left to stir for 5 h. The solution was purged with Ar again and filtered through celite to remove the Pd/C. The solution was evaporated to give 3-aminobenzene sulfonamide (95%) which was used without further purification at the next step.

Step B. Preparation of 6-(3-Sulfamoylphenylazo)-pyridoxal-5-phosphate

This product was obtained from 3-aminobenzene sulfonamide (step A) and pyridoxal-5-phosphate as described in general procedure D, method A. The desired material was obtained in 22% yield.

$^1$H NMR (D$_2$O): δ 2.27 (s, 3H), 5.52 (s, 2H), 7.56 (t, J=7.1, 1H), 7.77 (t, J=7.1, 1H), 7.93 (t, J=7.1, 1H), 8.10 (s, 1H), 10.23 (s, 1H). $^{31}$P NMR (D$_2$O): δ 6.99 (s).

Example 36

Preparation of 6-[3-(2-(1,4,5,6-Tetrahydropyrimidyl)carbamoyl)phenylazo]-pyridoxal-5-phosphate Step A. Preparation of 3-Amino-N-(1,4,5,6-tetrahydropyrimidin-2-yl)-benzamide The coupling of pyrimidin-2-ylamine with m-nitrobenzoyl chloride was achieved using general procedure A (steps 1 and 2). The pyrimidine ring system was partly hydrogenated at step 2. The title product was used as such without further purification at the next step.

Step B. Preparation of 6-[3-(2-(1,4,5,6-Tetrahydropyrimidyl)carbamoyl)phenylazo]-pyridoxal-5-phosphate This compound was prepared from 3-amino-N-(1,4,5,6-tetrahydropyrimidin-2-yl)-benzamide (step A) and pyridoxal-5-phosphate as described in general procedure D, method A. The final product was obtained in 8% yield.

$^1$H NMR (D$_2$O): δ 1.68–1.81 (m, 4H), 2.22 (s, 3H), 2.56 (t, J=5.3, 2H), 5.44 (br s, 2H), 6.85–6.89 (m 2H), 7.70–7.8 (m, 2H), 8.11 (s 1H), 10.16 (br s, 1H). $^{31}$P NMR (D$_2$O): δ 6.78 (s).

Example 37

Preparation of 6-[3-(5-(1,2,3,4-Tetrahydroquinolyl) carbamoyl)phenylazo]-pyridoxal-5-phosphate Step A. Preparation of 3-Amino-N-(1,2,3,4-tetrahydroquinolin-5-yl)-benzamide The coupling of quinolin-5-ylamine with m-nitrobenzoyl chloride was achieved using general procedure A (steps 1 and 2). The quinoline ring system was partly hydrogenated at step 2. The title product was used as such without further purification at the next step.

Step B. Preparation of 6-[3-(5-(1,2,3,4-Tetrahydroquinolyl) carbamoyl)phenylazo]-pyridoxal-5-phosphate This derivative was prepared from 3-amino-N-(1,2,3,4-tetrahydroquinolin-5-yl)-benzamide (step A) and pyridoxal-5-phosphate as described in general procedure D, method A. The final product was obtained in 10% yield.

$^1$H NMR (D$_2$O): δ 1.81 (t, J=5.2, 2H), 2.22 (s, 3H), 2.56 (t, J=5.3, 2H), 3.75 (t, J=5.2, 2H), 5.44 (br s, 2H), 6.85–6.89 (m, 2H), 7.12 (t, J=7.1, 1H), 7.42 (t, J=7.1, 1H), 7.64 (d, J=7.4 1H), 7.78 (d, J=7.5, 1H), 8.11 (s, 1H), 10.16 (brs, 1H). $^{31}$P NMR (D$_2$O): δ 6.68 (s).

Example 38

Preparation of 6-(5-Carboxy-2-methylphenylazo)-pyridoxal-5-phosphate

This product was obtained from commercially available 3-amino-4-methyl benzoic acid and pyridoxal-5-phosphate as described in general procedure D, method A. The final product was obtained in 23% yield.

$^1$H NMR (D$_2$O): δ 2.28 (s, 3H), 2.56 (s, 3H), 5.54 (s, 2H), 7.34 (d, J=7.2, 1H), 7.73 (d, J=7.2, 1H), 7.96 (s, 1H), 10.23 (s, 1H). $^{31}$P NMR (D$_2$O): δ 6.94 (s).

Example 39

Preparation of 6-(3-Carboxy-2-chlorophenylazo)-pyridoxal-5-phosphate

The title compound was obtained from commercially available 3-amino-2-chlorobenzoic acid and pyridoxal-5- phosphate as described in general procedure D, method A. The final product was obtained in 21% yield.

$^1$H NMR (D$_2$O): δ 2.30 (s, 3H), 5.65 (s, 2H), 7.21 (t, J=5.1, 2H), 7.77 (d, J=5.1, 2H), 10.29 (s, 1H). $^{31}$P NMR (D$_2$O): δ 7.00 (s).

Example 40

Preparation of 6-(5-Carboxy-2-chlorophenylazo)-pyridoxal-5-phosphate

This product was obtained from commercially available 3-amino-4-chlorobenzoic acid and pyridoxal-5-phosphate as described in general procedure D, method A. The final product was obtained in 21% yield.

$^1$H NMR (D$_2$O): δ 2.30 (s, 3H), 5.65 (s, 2H), 7.56 (s, 1H), 7.88–7.91 (m, 2H), 10.26 (s, 1H). $^{31}$P NMR (D$_2$O): δ 7.02 (s).

Example 41

Preparation of 6-(3-Carboxy-2,4,5-trifluorophenylazo)-pyridoxal-5-phosphate

The title compound was obtained from commercially available 3-amino-2,5,6-trifluorobenzoic acid and pyridoxal-5-phosphate as described in general procedure D, method A. The final product was obtained in 11% yield.

$^1$H NMR (D$_2$O): δ 2.30 (s, 3H), 5.65 (s, 2H), 7.72 (s, 1H), 10.16 (s, 1H). $^{31}$P NMR (D$_2$O): δ 7.02 (s).

Example 42

Preparation of 6-(4-Cyanophenylazo)-pyridoxal-5-phosphate

This product was obtained from commercially available 4-amino-benzonitrile and pyridoxal-5-phosphate as described in general procedure D, method A. The final product was obtained in 41% yield.

$^1$H NMR (D$_2$O): δ 2.30 (s, 3H), 5.65 (s, 2H), 7.86 (d, J=7.1, 2H), 7.94 (d, J=7.1, 2H), 10.30 (s, 1H). $^{31}$P NMR (D$_2$O): δ 7.02 (s).

Example 43

Preparation of 6-(4-Carbamoylphenylazo)-pyridoxal-5-phosphate

The title compound was obtained from commercially available 4-aminobenzamide and pyridoxal-5-phosphate as described in general procedure D, method A. The final product was obtained in 15% yield.

$^1$H NMR (D$_2$O): δ 2.30 (s, 3H), 5.65 (s, 2H), 7.86 (d, J=7.1, 2H), 7.94 (d, J=7.1, 2H), 10.30 (s, 1H). $^{31}$P NMR (D$_2$O): δ 7.00 (s).

Example 44

Preparation of 6-[4-(2-Fluorophenylsulfamoyl)phenylazo]pyridoxal-5-phosphate
Step A. Preparation of 4-Amino-N-(2-fluorophenyl)-benzenesulfonamide
The coupling of 2-fluoroaniline with p-acetamidobenzenesulfonyl chloride was achieved using general procedure B (steps 1 and 2). The title product was used as such without further purification at the next step.
Step B. Preparation of 6-[4-(2-Fluorophenylsulfamoyl)phenylazo]-pyridoxal-5-phosphate
The title compound was prepared from 4-amino-N-(2-fluorophenyl)-benzenesulfonamide (step A) and pyridoxal-5-phosphate as described in general procedure D, method A. The final product was obtained in 42% yield.

$^1$H NMR (D$_2$O): δ 2.26 (s, 3H), 5.49 (br s, 2H), 6.75–6.94 (m, 4H), 7.79 (d, J=7.9, 4H), 7.86 (d, J=7.9, 2H), 10.23 (s, 1H). $^{31}$P NMR (D$_2$O): δ 6.97 (s).

Example 45

Preparation of 6-[4-(3-Fluorophenylsulfamoyl)phenylazo]-pyridoxal-5-phosphate

This compound was prepared as described for the preparation of the analogue 6-[4-(2-fluorophenylsulfamoyl)phenylazo]-pyridoxal-5-phosphate (see example 44, steps A and B) using 3-fluoroaniline instead of 2-fluoroaniline. The title compound was obtained in 57% yield.

$^1$H NMR (D$_2$O): δ 2.26 (s, 3H), 5.49 (br s, 2H), 6.47–6.59 (m, 3H), 6.99 (s, 1H), 7.80 (d, J=7.9, 4H), 7.86 (d, J=7.9, 2H), 10.23 (s, 1H). $^{31}$P NMR (D$_2$O): δ 6.92 (s).

Example 46

Preparation of 6-[4-(4-Fluorophenylsulfamoyl)phenylazo]-pyridoxal-5-phosphate

This compound was prepared as described for the preparation of the analogue 6-[4-(2-fluorophenylsulfamoyl)phenylazo]-pyridoxal-5-phosphate (see example 44, steps A and B) using 4-fluoroaniline instead of 2-fluoroaniline. The title compound was obtained in 54% yield.

$^1$H NMR (D$_2$O): δ 2.46 (s, 3H), 5.75 (br s, 2H), 7.07 (s, 4H), 7.70 (br s, 2H), 8.07 (br s, 2H), 10.46 (s, 1H). $^{31}$P NMR (D$_2$O): δ 7.02 (s).

Example 47

Preparation of 6-(2,3-Dicarboxyphenylazo)-pyridoxal-5-phosphate

This product was obtained from commercially available 3-aminophthalic acid and pyridoxal-5-phosphate as described in general procedure D, method A. The desired material was obtained in 30% yield.

$^1$H NMR (D$_2$O): δ 2.21 (s, 3H), 5.45 (s, 2H), 7.22 (t, J=4,5, 1H), 7.56 (d, J=5.0, 1H), 7.72 (d, J=5.0 1H), 10.06 (s, 1H). $^{31}$P NMR (D$_2$O): δ 6.99 (s).

Example 48

Preparation of 6-(2-Carboxyphenylazo)-pyridoxal-5-phosphate

This derivative was obtained from commercially available anthranilic acid and pyridoxal-5-phosphate as described in general procedure D, method A. The title compound was obtained in 31% yield.

$^1$H NMR (D$_2$O): δ 2.30 (s, 3H), 5.65 (s, 2H), 7.33 (s, 1H), 7.51 (s, 2H), 7.86 (s, 1H), 10.30 (s, 1H). $^{31}$P NMR (D$_2$O): δ 6.37 (s).

Example 49

Preparation of 6-(3,5-Dicarboxyphenylazo)-pyridoxal-5-phosphate Methanesulfonic Acid Salt This material was prepared following the procedure described for the preparation of 6-(3,5-dicarboxyphenylazo)-pyridoxal-5-phosphate (example 22) using methanesulfonic acid for the acidification step instead of hydrochloric acid. The desired material was obtained in 55% yield.

$^1$H NMR (D$_2$O): δ 2.30 (s, 3H), 2.45 (s, 3H), 2.67 (s, 3H), 5.65 (s, 2H), 8.21 (s, 1H), 8.32 (s, 2H), 10.26 (s, 1H). $^{31}$P NMR (D$_2$O): δ 7.02 (s).

Example 50

Preparation of 6-(3,5-Dicarboxyphenylazo)-pyridoxal-5-phosphate Penta-potassium Salt This product was obtained from 6-(3,5-dicarboxyphenylazo)-pyridoxal-5-phosphate (example 22) as described in general procedure D, method B. The desired material was obtained in 60% yield.

$^1$H NMR (D$_2$O): δ 2.30 (s, 3H), 5.65 (s, 2H), 8.21 (s, 1H), 8.32 (s, 2H), 10.26 (s, 1H). $^{31}$P NMR (D$_2$O): δ 7.02 (s).

Example 51

Preparation of 6-(3,5-Dicarboxyphenylazo)-pyridoxal-5-phosphate Diethylacetal This compound was obtained from 6-(3,5-dicarboxyphenylazo)-pyridoxal-5-phosphate phosphate penta-potassium salt (example 50) as described in general procedure E. The desired material was obtained in 90% yield.

$^1$H NMR (DMSO-d$_6$): δ 1.05 (t, J=6.1, 6H), 2.35 (s, 3H), 3.68–3.91 (m, 4H), 5.55 (s,2H), 6.20 (s, 1H), 8.52–8.54 (m, 3H). $^{31}$P NMR (DMSO-d$_6$): δ 6.02 (s).

Example 52

Preparation of 6-(3,5-Dicarboxyphenylazo)-pyridoxal-5-phosphate Oxime

This product was obtained from 6-(3,5-dicarboxyphenylazo)-pyridoxal-5-phosphate (example 22) as described in general procedure F. The desired material was obtained in 34% yield.

$^1$H NMR (D$_2$O): δ 2.30 (s, 3H), 5.65 (s, 2H), 8.03 (s, 1H), 8.21 (s, 1H), 8.27 (s, 2H). $^{31}$P NMR (D$_2$O): δ 7.00 (s).

Example 53

Preparation of 6-[4-(2-Pyrimidylsulfamoyl)phenylazo]-pyridoxal-5-phosphate Oxime This derivative was obtained from 6-[4-(2-pyrimidylsulfamoyl)phenylazo]-pyridoxal-5-phosphate (example 25) as described in general procedure F. The desired material was obtained in 5% yield.

$^1$H NMR (D$_2$O): δ 2.20 (s, 3H), 5.45 (s, 2H), 6.76–6.88 (m, 3H), 6.96 (s, 1H), 7.87 (s, 4H).

BIOLOGICAL EVALUATION

Integrase Inhibition Assay in vitro

For the purpose of Table 1, the HIV-1 integrase inhibition assay was carried out following a known procedure (Burke, Jr. T. R. et al., J. Med. Chem. 38, 4171–4178 (1995)). A suitable radiolabeled duplex substrate corresponding to the U5 end of the HIV LTR was used.

Anti-viral and Cytotoxicity Assays in vitro

To evaluate the EC$_{50}$ of our compounds, various drug concentrations are incubated with the infected cell for six days and then the metabolic activity of the cells is monitored by the MTT assay. (See A. J. Japour et al, Antimicrobial Agents and Chemotherapy, 37, 1095–1101, 1993 and R. Pauwels et al. Journal of Virological Methods, 20, 309–321, 1988).

We use the laboratory viral strain NL4.3 as wild type virus and the cell line used is MT-4 which is a T-cell line highly sensitive to HIV-1. We also use some WT clinical strains. To address the resistance issue we assay the inhibitors with NL4.3 mutants which are designed to be resistant to specific commercially available inhibitors. The following reagents were obtained through the AIDS Research and Reference Reagent Program, division of AIDS, NIAID, NIH: pNL4.3 from Dr. Malcolm Martin; MT-4 cell line from Dr. Douglas Richman. Wild type (WT) clinical strains were obtained from "Laboratoire de santé publique du Québec".

The same MTT assay is used to evaluate the CCIC$_{50}$ of our compounds except that the virus is omitted.

The compounds listed in Table 1 were prepared by following Scheme 1, 2, 3 or 4; and more particularly as described in each example listed above. The numbers of the compounds listed in Table 1 (Ex. No.) correspond to the example numbers presented above. The activities of the compounds are also listed in the same table, i.e. demonstrating their usefulness. In Table 1 are shown compounds of formula I wherein carbon 2', 3', 4', 5' and in a case 6' (i.e. for compound no. 38) are substituted as presented in Table 1. IC$_{50}$, EC$_{50}$ as well as CCIC$_{50}$ results for compound of formula I are also presented in Table 1 illustrating their potential usefulness.

TABLE 1

Anti-integrase activity of pyridoxal-5-phosphate derivatives of formula I and analogs

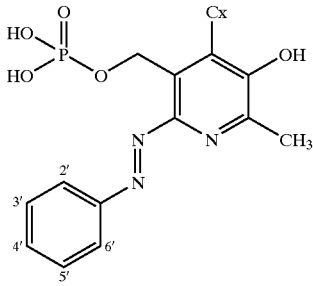

I

| Ex. No. | Cx | 2' | 3' | 4' | 5' | IC$_{50}$ (nM) | EC$_{50}$ (nM) | CCIC$_{50}$ (nM) |
|---|---|---|---|---|---|---|---|---|
| 1 | CHO | CH$_3$ | COOH | H | H | 1200 | 2000 | >100000 |
| 2 | CHO | H | H | SO$_2$NH$_2$ | H | 250 | 5000 | >100000 |

TABLE 1-continued

Anti-integrase activity of pyridoxal-5-phosphate derivatives of formula I and analogs

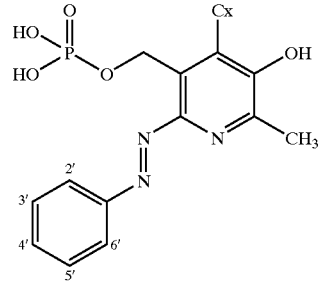

I

| Ex. No. | Cx | 2' | 3' | 4' | 5' | IC$_{50}$ (nM) | EC$_{50}$ (nM) | CCIC$_{50}$ (nM) |
|---|---|---|---|---|---|---|---|---|
| 3 | CHO | H | H | SO$_2$NH—(N-(adamantan-1-yl)) | H | 200 | 19800 | 12000 |
| 4 | CHO | H | CONH—(N-(adamantan-1-yl)) | H | H | 400 | 50000 | 13000 |
| 5 | CHO | H | H | SO$_2$N—(N-isobutyl)-(N-(ε-caprolactam-2-yl)) | H | 600 | 17000 | >100000 |
| 6 | CHO | H | SO$_2$-(piperidin-1-yl) | H | H | 4370 | ND | ND |
| 7 | CHO | H | H | SO$_2$-(piperidin-1-yl) | H | 2500 | 12500 | >100000 |
| 8 | CHO | H | CO-(piperidin-1-yl) | H | H | 2800 | ND | ND |
| 9 | CHO | H | SO$_2$NH—(N-tert-butyl) | H | H | 3000 | 15000 | 57000 |
| 10 | CHO | H | H | SO$_2$NH—(N-tert-butyl) | H | 4250 | ND | ND |
| 11 | CHO | H | H | CONH—(N-tert-butyl) | H | 2730 | ND | ND |
| 12 | CHO | H | SO$_2$-(pyrrolidin-1-yl) | H | H | 2900 | ND | ND |
| 13 | CHO | H | CONH—(N-isobutyl) | H | H | 1300 | 50000 | 90000 |
| 14 | CHO | H | H | CONH—(N-cyclohexyl) | H | 4360 | ND | ND |
| 15 | CHO | H | H | SO$_2$-(pyrrolidin-1-yl) | H | 1700 | ND | ND |
| 16 | CHO | H | SO$_2$NH—(N-isobutyl) | H | H | 1900 | ND | ND |
| 17 | CHO | H | H | SO$_2$NH—(N-isobutyl) | H | 2450 | ND | ND |
| 18 | CHO | H | H | SO$_2$NH—(N-cyclohexyl) | H | 2200 | ND | ND |
| 19 | CHO | H | SO$_2$NH—(N-butyl) | H | H | 2000 | ND | ND |
| 20 | CHO | H | H | SO$_2$NH—(N—CH$_3$) | H | 1200 | ND | ND |
| 21 | CHO | H | SO$_2$NH—(N—CH$_2$CH$_2$OH) | H | H | 2450 | ND | ND |
| 22 | CHO | H | COOH | H | COOH | 430 | ND | >100000 |
| 23 | CHO | H | H | SO$_2$NH—(N-(2,6-dimethylpyrimidin-4-yl)) | H | 2750 | ND | ND |
| 24 | CHO | H | H | SO$_2$NH—(N-thiazol-2-yl) | H | 365 | 23000 | >100000 |
| 25 | CHO | H | H | SO$_2$NH—(N-pyrimidin-2-yl) | H | 300 | 4300 | >100000 |
| 26 | CHO | H | SO$_2$NH—(N—CH$_3$) | H | H | 3700 | ND | ND |
| 27 | CHO | H | SO$_2$-(morpholin-4-yl) | H | H | 1100 | 27500 | >100000 |
| 28 | CHO | H | CONH—(N-pyridin-3-yl) | H | H | 3250 | 6250 | 50000 |
| 29 | CHO | H | CONH—(N-pyridin-2-yl) | H | H | 3850 | 24000 | >100000 |
| 30 | CHO | H | CONH—(N-pyridin-4-yl) | H | H | 3150 | 20000 | 87000 |
| 31 | CHO | H | CONH—(N-isoquinolin-5-yl) | H | H | 3250 | 15000 | >100000 |
| 32 | CHO | H | H | SO$_2$NH—(N-isoazol-3-yl) | H | 3000 | 50000 | ND |
| 33 | CHO | NO$_2$ | H | H | H | 5250 | 33000 | ND |
| 34 | CHO | H | Cl | H | H | 2600 | 45000 | ND |
| 35 | CHO | H | SO$_2$NH$_2$ | H | H | 12850 | ND | ND |
| 36 | CHO | H | CONH—(N-(1,4,5,6-tetrahydropyrimidin-2-yl) | H | H | 6200 | ND | ND |
| 37 | CHO | H | CONH—(N-(1,2,3,4-tetrahydroquinolin-5-yl) | H | H | 3300 | 26000 | 84000 |
| 38* | CHO | H | COOH (and 6'-CH$_3$) | H | H | 2300 | 50000 | >100000 |
| 39 | CHO | Cl | COOH | H | H | 2600 | 1800 | >100000 |
| 40 | CHO | Cl | H | COOH | H | 3350 | 17000 | >100000 |
| 41 | CHO | F | COOH | F | F | 2000 | 14000 | >100000 |
| 42 | CHO | H | H | CN | H | 11300 | ND | >100000 |
| 43 | CHO | H | H | CONH$_2$ | H | 8700 | ND | ND |
| 44 | CHO | H | H | SO$_2$NH—(N-(2-fluorophenyl)) | H | 7700 | ND | ND |
| 45 | CHO | H | H | SO$_2$NH—(N-(3-fluorophenyl)) | H | 10450 | ND | ND |
| 46 | CHO | H | H | SO$_2$NH—(N-(4-fluorophenyl)) | H | 1500 | ND | 32000 |
| 47 | CHO | COOH | COOH | H | H | 165 | 10000 | 17000 |
| 48 | CHO | COOH | H | H | H | 345 | >20000 | >100000 |
| 49** | CHO | H | COOH | H | COOH | 500 | 275 | 12000 |
| 50 | CHO | H | COOK | H | COOK | 470 | 5000 | >100000 |
| 51 | CH(OCH$_2$CH$_3$)$_2$ | H | COOH | H | COOH | 125 | 350 | >100000 |

TABLE 1-continued

Anti-integrase activity of pyridoxal-5-phosphate derivatives of formula I and analogs

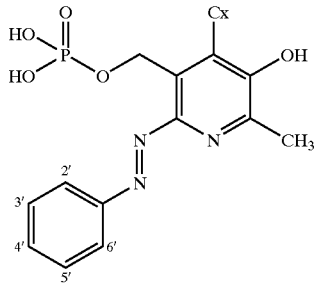

I

| Ex. No. | Cx | 2' | 3' | 4' | 5' | IC$_{50}$ (nM) | EC$_{50}$ (nM) | CCIC$_{50}$ (nM) |
|---|---|---|---|---|---|---|---|---|
| 52 | CH=NOH | H | COOH | H | COOH | 8750 | 15000 | 60000 |
| 53 | CH=NOH | H | H | SO$_2$NH—(N-pyrimidin-2-yl) | H | 2000 | 15000 | ND |

*(and at 6' has a —CH$_3$)
**Methanesulfonic acid salt

We claim:

1. A compound of formula I

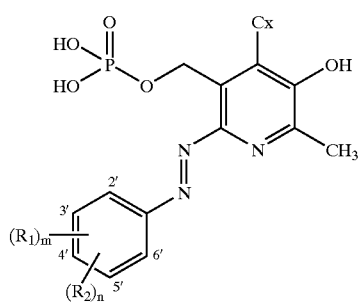

I wherein Cx is selected from the group consisting of —CH=O, —CH=N—OH and —CH(OCH$_2$CH$_3$)$_2$, wherein R$_1$ is selected from the group consisting of H, a straight alkyl group of 1 to 6 carbon atoms, a branched alkyl group of 3 to 6 carbon atoms, F, Cl, Br, I, —CN and —COOH, wherein R$_2$ is selected from the group consisting of —COOH, —SO$_2$NR$_3$R$_4$, —SO$_2$R$_5$, —CONR$_3$R$_4$ and —COR$_5$, wherein R$_3$ is selected from the group consisting of H, a straight alkyl group of 1 to 6 carbon atoms, and a branched alkyl group of 3 to 6 carbon atoms, wherein R$_4$ is selected from the group consisting of H, a straight alkyl group of 1 to 6 carbon atoms, a branched alkyl group of 3 to 6 carbon atoms, a cycloalkyl group of 3 to 8 carbon atoms, adamantan-1-yl, —CH$_2$CH$_2$OH, pyridin-2-yl, pyridin-3-yl, pyridin-4-yl, 1,2,3,4-tetrahydroquinolin-5-yl, isoquinolin-5-yl, isoazol-3-yl, 2-halogeno-phenyl, 3-halogeno-phenyl, 4-halogeno-phenyl (halogeno being F, Cl, Br or I), 1,4,5,6-tetrahydropyrimidin-2-yl, pyrimidin-2-yl, 2,6-dimethylpyrimidin-4-yl, thiazol-2-yl and a group of formula

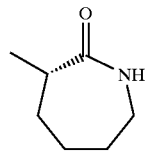

wherein R$_5$ is selected from group consisting of aziridin-1-yl, azetidin-1-yl, pyrrolidin-1-yl, piperidin-1-yl, azepan-1-yl, azocanyl (i.e., the azacycloalkanes, 3 to 8 member ring system) and morpholin-4-yl, wherein m is 0, 1, 2 or 3, wherein n is 0 or 1, provided that when Cx is —CH=O and R$_1$ is H or m is 0, n cannot be 0, provided that when Cx is —CH=O, R$_1$ is Cl, m is 1 and n is 0, R$_1$ is in a position selected from the group consisting of the 3', 4' and 5' position, provided that when Cx is —CH=O and R$_1$ is —COOH, m is 1 and n is 0, R$_1$ is in a position selected from the group consisting of the 2' and 6' position, provided that when Cx is —CH=O, R$_1$ is Cl, m is 1, n is 1, and R$_2$ is —COOH;
 R$_1$ may not occupy the 3' position when R$_2$ occupies a position selected from the group consisting of 2' and 4' position, and;
 R$_1$ may not occupy the 2' position when R$_2$ occupies a 5' position.

2. A compound as defined in claim 1, wherein Cx is —CHO, m is 0 and n is 1.

3. A compound as defined in claim 1, wherein Cx is —CHO, m is 1 and n is 1.

4. A compound as defined in claim 3, wherein R$_1$ is —CH$_3$ and R$_2$ is —CO$_2$H.

5. A compound as defined in claim 3, wherein R$_1$ is —CO$_2$H and R$_2$ is —CO$_2$H.

6. A compound as defined in claim 3, wherein R$_1$ is Cl and R$_2$ is —CO$_2$H.

7. A compound as defined in claim 5, wherein R$_1$ is —CO$_2$H at position 3' and R$_2$ is —CO$_2$H at position 5'.

8. A compound as defined in claim 6, wherein R$_1$ is Cl at position 2', R$_2$ is —CO$_2$H at position 3'.

9. A compound of formula IA

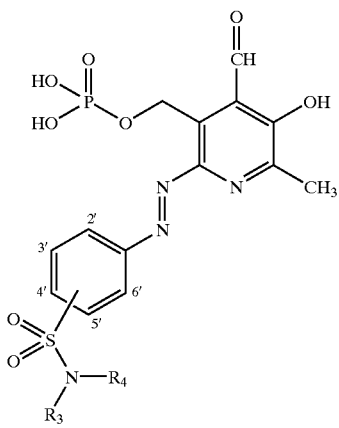

wherein R₃ is selected from the group consisting of H, a straight alkyl group of 1 to 6 carbon atoms, and a branched alkyl group of 3 to 6 carbon atoms, and
wherein R₄ is selected from the group consisting of H, a straight alkyl group of 1 to 6 carbon atoms, a branched alkyl group of 3 to 6 carbon atoms, a cycloalkyl group of 3 to 8 carbon atoms, adamantan-1-tyl, —CH₂CH₂OH, pyridin-2-yl, pyridin-3-yl, pyridin-4-yl, 1,2,3,4-tetrahydroquinolin-5-yl, isoquinolin-5-yl, isoazol-3-yl, 2-halogeno-phenyl, 3-halogeno-phenyl, 4-halogeno-phenyl (halogeno being F, Cl, Br or I), 1,4,5,6-tetrahydropyrimidin-2-yl, pyrimidin-2-yl, 2,6-dimethylpyrimid-4-yl, thiazol-2-yl and a group of formula

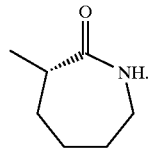

10. A compound as defined in claim 9, wherein the sulfonamide group, —SO₂NR₃R₄, is located at position 3'.
11. A compound as defined in claim 9, wherein the sulfonamide group, —SO₂NR₃R₄, is located at position 4'.
12. A compound of formula IB

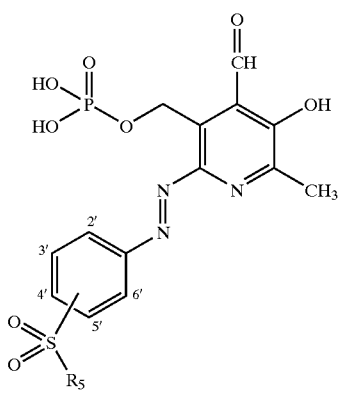

wherein R₅ is selected from the group consisting of pyrrolidin-1-yl, piperidin-1-yl and morpholin-4-yl.
13. A compound as defined in claim 12, wherein the group, —SO₂R₅, is located at position 3'.
14. A compound as defined in claim 12, wherein the group, —SO₂R₅, is located at position 4'.

15. A compound of formula IC

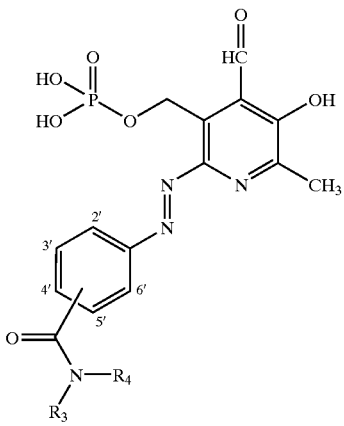

wherein R₃ is selected from the group consisting of H, a straight alkyl group of 1 to 6 carbon atoms, and a branched alkyl group of 3 to 6 carbon atoms, and
wherein R₄ is selected from the group consisting of H, a straight alkyl group of 1 to 6 carbon atoms, a branched alkyl group of 3 to 6 carbon atoms, a cycloalkyl group of 3 to 8 carbon atoms, adamantan-1-yl, —CH₂CH₂OH, pyridin-2-yl, pyridin-3-yl, pyridin-4-yl, 1,2,3,4-tetrahydroquinolin-5-yl, isoquinolin-5-yl, isoazol-3-yl, 2-halogeno-phenyl, 3-halogeno-phenyl, 4-halogeno-phenyl (halogeno being F, Cl, Br or I), 1,4,5,6-tetrahydropyrimidin-2-yl, pyrimidin-2-yl, 2,6-dimethylpyrimidin-4-yl, thiazol-2-yl and a group of formula

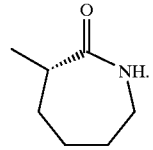

16. A compound as defined in claim 15, wherein the amide group, —CONR₃R₄, is located at position 3'.
17. A compound as defined in claim 15, wherein the amide group, —CONR₃R₄, is located at position 4'.
18. A compound of formula ID

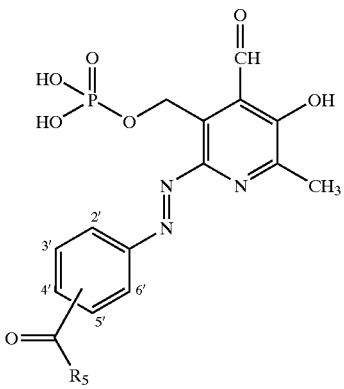

wherein R₅ is selected from the group consisting of pyrrolidin-1-yl, piperidin-1-yl and morpholin-4-yl.
19. A compound as defined in claim 18, wherein the group, —COR₅, is located at position 3'.

20. A compound as defined in claim 18, wherein the group, —COR$_5$, is located at position 4'.

21. A compound as defined in claim 11, wherein R$_3$ is H and R$_4$ is H.

22. A compound as defined in claim 11, wherein R$_3$ is H and R$_4$ is pyrimid-4-yl.

23. A compound as defined in claim 7 as its methanesulfonic acid salt.

24. A compound as defined in claim 7 as its pentapotassium salt.

25. A compound as defined in claim 1, wherein Cx is —CH(OCH$_2$CH$_3$)$_2$, R$_1$ is —CO$_2$H at position 3', R$_2$ is —CO$_2$H at position 5', m is 1 and n is 1.

26. A pharmaceutical composition comprising a pharmaceutically acceptable carrier and at least one compound as defined in claim 1.

27. A pharmaceutical composition comprising a pharmaceutically acceptable carrier and at least one compound of formula I'

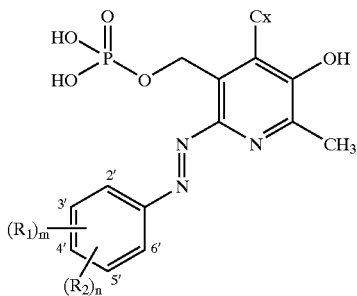

wherein Cx is selected from the group consisting of —CH=O, —CH=N—OH and —CH(OCH$_2$CH$_3$)$_2$,
  wherein R$_1$ is selected from the group consisting of H, a straight alkyl group of 1 to 6 carbon atoms, a branched alkyl group of 3 to 6 carbon atoms, F, Cl, Br, I, —CN and —COOH, wherein R$_2$ is selected from the group consisting of —COOH, —SO$_2$NR$_3$R$_4$, —SO$_2$R$_5$, —CONR$_3$R$_4$ and —COR$_5$,
  wherein R$_3$ is selected from the group consisting of H, a straight alkyl group of 1 to 6 carbon atoms, and a branched alkyl group of 3 to 6 carbon atoms,
  wherein R$_4$ is selected from the group consisting of H, a straight alkyl group of 1 to 6 carbon atoms, a branched alkyl group of 3 to 6 carbon atoms, a cycloalkyl group of 3 to 8 carbon atoms, adamantan-1-yl, —CH$_2$CH$_2$OH, pyridin-2-yl, pyridin-3-yl, pyridin-4-yl, 1,2,3,4-tetrahydroquinolin-5-yl, isoquinolin-5-yl, isoazol-3-yl, 2-halogeno-phenyl, 3-halogeno-phenyl, 4-halogeno-phenyl (halogeno being F, Cl, Br or I), 1,4,5,6-tetrahydropyrimidin-2-yl, pyrimidin-2-yl, 2,6-dimethylpyrimidin-4-yl, thiazol-2-yl and a group of formula

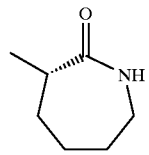

wherein R$_5$ is selected from group consisting of aziridin-1-yl, azetidin-1-yl, pyrrolidin-1-yl, piperidin-1-yl, azepan-1-yl, azocanyl (i.e., the azacycloalkanes, 3 to 8 member ring system) and morpholin-4-yl, and wherein m is 0, 1, 2 or 3, wherein n is 0 or 1.

28. A pharmaceutical composition as defined in claim 27, wherein Cx is —CHO, m is 0 and n is 1.

29. A pharmaceutical composition as defined in claim 27, wherein Cx is —CHO, m is 1 and n is 1.

30. A pharmaceutical composition as defined in claim 29, wherein R$_1$ is —CH$_3$ and R$_2$ is —CO$_2$H.

31. A pharmaceutical composition as defined in claim 29, wherein R$_1$ is —CO$_2$H and R$_2$ is —CO$_2$H.

32. A pharmaceutical composition as defined in claim 29, wherein R$_1$ is Cl and R$_2$ is —CO$_2$H.

33. A pharmaceutical composition as defined in claim 31, wherein R$_1$ is —CO$_2$H at position 3' and R$_2$ is —CO$_2$H at position 5'.

34. A pharmaceutical composition as defined in claim 32, wherein R$_1$ is Cl at position 2', R$_2$ is —CO$_2$H at position 3'.

35. A pharmaceutical composition comprising a pharmaceutically acceptable carrier and at least one compound of formula IA as defined in claim 9.

36. A pharmaceutical composition comprising a pharmaceutically acceptable carrier and at least one compound of formula IB as defined in claim 12.

37. A pharmaceutical composition comprising a pharmaceutically acceptable carrier and at least one compound of formula IC as defined in claim 15.

38. A pharmaceutical composition comprising a pharmaceutically acceptable carrier and at least one compound of formula ID as defined in claim 18.

* * * * *

UNITED STATES PATENT AND TRADEMARK OFFICE
CERTIFICATE OF CORRECTION

PATENT NO. : 6,638,921 B1
DATED : October 28, 2003
INVENTOR(S) : Brent Richard Stranix and Gilles Sauvé

It is certified that error appears in the above-identified patent and that said Letters Patent is hereby corrected as shown below:

Column 20,
Line 3, the phrase "(N-(2-E-Caprolactamyl)" should read -- (N-(2-ε-Caprolactamyl) --;
Line 8, the phrase "(N-(2-F-Caprolactamyl)" should read -- (N-(2-ε-Caprolactamyl) --;

Column 24,
Line 33, the phrase "in-nitrobenzenesulfonyl" should read -- m-nitrobenzenesulfonyl --;

Column 38,
Lines 35 and 36, the phrase "(i.e., the azacycloalkanes, 3 to 8 member ring system)" should be deleted, and;

Column 42,
Lines 18 and 19, the phrase "(i.e., the azacycloalkanes, 3 to 8 member ring system" should be deleted.

Signed and Sealed this

First Day of June, 2004

JON W. DUDAS
*Acting Director of the United States Patent and Trademark Office*